United States Patent
Ballantine et al.

(10) Patent No.: US 9,859,580 B2
(45) Date of Patent: Jan. 2, 2018

(54) STRUCTURE AND METHOD FOR INDICATING UNDESIRABLE CONSTITUENTS IN A FUEL CELL SYSTEM

(71) Applicant: BLOOM ENERGY CORPORATION, Sunnyvale, CA (US)

(72) Inventors: Arne Ballantine, Palo Alto, CA (US); David Trevisan, San Jose, CA (US); Venkat Ramani, Sunnyvale, CA (US); Emma Campbell, Sunnyvale, CA (US); Jessica Mahler, Mountain View, CA (US); Michael Wright, Sunnyvale, CA (US); Jeffrey W. Schrieber, Sunnyvale, CA (US)

(73) Assignee: BLOOM ENERGY CORPORATION, Sunnyvale, CA (US)

( * ) Notice: Subject to any disclaimer, the term of this patent is extended or adjusted under 35 U.S.C. 154(b) by 0 days.

(21) Appl. No.: 14/589,403

(22) Filed: Jan. 5, 2015

(65) Prior Publication Data
US 2015/0194685 A1 Jul. 9, 2015

Related U.S. Application Data

(60) Provisional application No. 61/923,886, filed on Jan. 6, 2014.

(51) Int. Cl.
*H01M 8/04089* (2016.01)
*H01M 8/04746* (2016.01)
(Continued)

(52) U.S. Cl.
CPC ........ *H01M 8/04753* (2013.01); *G01N 33/52* (2013.01); *H01M 8/0444* (2013.01);
(Continued)

(58) Field of Classification Search
CPC ..................... H01M 8/04089; H01M 8/04208
See application file for complete search history.

(56) References Cited

U.S. PATENT DOCUMENTS 6,429,019 B1 * 8/2002 Goldstein ............ G01N 33/004
422/111
7,067,208 B2 6/2006 Gottmann et al.
(Continued)

FOREIGN PATENT DOCUMENTS

| CA | 2653441 A1 | 1/2008 |
|---|---|---|
| EP | 0817298 A1 | 1/1998 |
| EP | 2510572 B1 | 10/2012 |

OTHER PUBLICATIONS

International Search Report and Written Opinion received in connection with international application No. PCT/US2015/010137; dated Apr. 30, 2015.
(Continued)

*Primary Examiner* — Olatunji Godo
(74) *Attorney, Agent, or Firm* — The Marbury Law Group PLLC

(57) ABSTRACT

An optical detection system for detecting undesirable constituents in a fuel cell system includes a sensing material configured to change color in the presence of the undesirable constituents and at least one sensor configured to register the change in color of the sensing material. The sensor is coupled to a corresponding light source. The sensing material, the sensor and the light source are enclosed in a housing.

16 Claims, 28 Drawing Sheets

(51) Int. Cl.

| | |
|---|---|
| *G01N 33/52* | (2006.01) |
| *H01M 8/0444* | (2016.01) |
| *H01M 8/0662* | (2016.01) |
| *H01M 8/12* | (2016.01) |
| *H01M 8/04082* | (2016.01) |
| *H01M 8/0438* | (2016.01) |
| *H01M 8/04537* | (2016.01) |
| *H01M 8/04664* | (2016.01) |
| *H01M 8/124* | (2016.01) |

(52) U.S. Cl.
 CPC ... *H01M 8/04089* (2013.01); *H01M 8/04201* (2013.01); *H01M 8/04388* (2013.01); *H01M 8/04447* (2013.01); *H01M 8/04559* (2013.01); *H01M 8/04686* (2013.01); *H01M 8/04776* (2013.01); *H01M 8/0662* (2013.01); *H01M 8/0675* (2013.01); *H01M 8/0687* (2013.01); *H01M 8/12* (2013.01); *H01M 2008/1293* (2013.01); *Y10T 436/18* (2015.01)

(56) References Cited

U.S. PATENT DOCUMENTS

| | | |
|---|---|---|
| 7,422,810 B2 | 9/2008 | Venkataraman et al. |
| 8,440,362 B2 | 5/2013 | Richards et al. |
| 8,535,836 B2 | 9/2013 | Ballantine et al. |
| 8,652,697 B2 | 2/2014 | Gottmann et al. |
| 9,190,693 B2 | 11/2015 | Sridhar et al. |
| 2003/0113598 A1 | 6/2003 | Chow et al. |
| 2004/0202908 A1 | 10/2004 | Schmitz et al. |
| 2006/0188763 A1 | 8/2006 | Bai et al. |
| 2007/0196704 A1 | 8/2007 | Valensa et al. |
| 2007/0224472 A1 | 9/2007 | Fujita et al. |
| 2008/0096087 A1 | 4/2008 | Kulakov |
| 2008/0213141 A1 | 9/2008 | Pinchot |
| 2008/0289496 A1 | 11/2008 | Poshusta et al. |
| 2009/0029208 A1* | 1/2009 | Katikaneni ....... H01M 8/04447 429/410 |
| 2009/0197296 A1 | 8/2009 | Martin et al. |
| 2010/0216628 A1 | 8/2010 | Vanderspurt et al. |
| 2011/0281185 A1 | 11/2011 | Sridhar et al. |
| 2014/0004433 A1 | 1/2014 | Ballantine et al. |

OTHER PUBLICATIONS

International Search Report & Written Opinion, International Application No. PCT/US2010/041238, dated Mar. 2, 2011.
International Preliminary Report on Patentability, International Application No. PCT/US2010/041238, dated Jan. 19, 2012.
European Office Communication Pursuant to Rules 161(2) and 162 PEC for European Patent Application No. 15733274.3, dated Sep. 6, 2016, 2 pages.
European Office Communication Pursuant to Rules 62 EPC and Supplementary European Search Report (Art. 153(7) EPC) and European Search Opinion for European Patent Application No. 15733274.3, dated Jun. 16, 2017, 7 pages.

* cited by examiner

1300

Providing an Optical Detection System Comprising a Sensing Material Configured to Change Color in the Presence of the Undesirable Constituents and at Least One Sensor Configured to Register the Change in Color of the Sensing Material, the Sensor Coupled to a Corresponding Light Source, wherein the Sensing Material, the Sensor and the Light Source Are Enclosed in a Housing
1302

Detecting an Undesirable Constituent in a Fuel Stream of the Fuel Cell System
1304

Generating an Alarm Signal when an Alarm Criterion is Met
1306

> Providing an Optical Detection System Comprising a Sensing Material Configured to Change Color in the Presence of the Undesirable Constituents and at Least One Sensor Configured to Register the Change in Color of the Sensing Material, the Sensor is Coupled to a Corresponding Light Source, a Reference Material that Does Not Change Color in the Presence of the Undesirable Constituents and a Reference Sensor Configured to Register the Change in Color of the Reference Material and Optically Coupled to a Light Source
> 1402

> Detecting an Undesirable Constituent in a Fuel Stream of the Fuel Cell System
> 1404

> Generating an Alarm Signal when an Alarm Criterion Is Met
> 1406

FIG. 14

STRUCTURE AND METHOD FOR INDICATING UNDESIRABLE CONSTITUENTS IN A FUEL CELL SYSTEM

RELATED APPLICATIONS

This application claims the benefit of priority to U.S. Provisional Patent Application No. 61/923,886 entitled "Structure and Method for Indicating Undesirable Constituents in a Fuel Cell System" filed Jan. 6, 2014, the entire contents of which are hereby incorporated by reference.

BACKGROUND

The reliability of fuel cell systems, such as a solid oxide fuel cell (SOFC) system, greatly depends on the presence and concentration of undesirable constituents in the fuel stream. Undesirable constituents, such as moisture, oxygen, siloxanes, and sulfur (including sulfur compounds), may degrade the fuel cell stack's performance and cause irreversible damage resulting in decrease efficiencies and costly replacement. Specifically, when using natural gas as a fuel, fuel cell systems require gas purification to remove, for example, sulfur and sulfur compounds, siloxanes, moisture, etc. Passing fuel through sorbent beds is one way to purify the natural gas from fuel prior to use in a fuel cell. However, sorbent beds (e.g., desulfurization adsorption beds) have a finite life and once the sorbent bed is exhausted, sulfur may pass through the sorbent bed without being absorbed and reach the fuel cell stack causing permanent damage. Even if sorbent beds are replaced prior to exhaustion, there may be underutilized portions of the sorbent bed increasing the cost of sorbent bed replacement. Additionally, other undesirable constituents not filtered by the gas purification sorbent beds may cause damage to the fuel cell stack shortening its operational life.

SUMMARY

Various embodiments provide an optical detection system for detecting undesirable constituents in a fuel cell system. The optical detection system may include a sensing material configured to change color in the presence of the undesirable constituents, and at least one sensor configured to register the change in color of the sensing material, in which the sensing material and the sensor are enclosed in a housing.

Some embodiments provide a method for detecting undesirable constituents in a fuel cell system by providing an optical detection system that includes a sensing material configured to change color in the presence of the undesirable constituents. Embodiment methods may include illuminating the sensing material with light from a light source, determining whether a change of color has occurred in the sensing material using a sensor, detecting a presence of an undesirable constituent in a fuel stream of the fuel cell system in response to determining that a change of color has occurred in the sensing material; and generating an alarm signal when an alarm criterion is met based on the presence of the undesirable constituent.

Embodiment methods may include providing an optical detection system that also includes at least one constituent sensor configured to register the change in color of the sensing material, a reference material configured to not change color in the presence of the undesirable constituents, and a reference sensor configured to register the change in color of the reference material. Embodiment methods may include detecting an undesirable constituent in a fuel stream of the fuel cell system based on a difference between a change of color of the sensing material and the reference material, and generating an alarm signal when an alarm criterion is met.

In various embodiment optical detection systems, the sensor may be coupled to a corresponding light source. Embodiment optical detection systems may also include a reference material that does not change color in the presence of the undesirable constituents, and a reference sensor configured to register the change in color of the reference material, in which the reference sensor is optically coupled to a light source.

Embodiment methods may include providing an optical detection system that also includes at least one sensor that includes red, green and blue color sensors, and a processor configured to receive color values from each color sensor. Embodiment methods may include sending individual values from each color sensor to the processor, and generating an alarm signal when an alarm criterion is met.

Various embodiments may include a fuel cell system with a fuel cell stack and a fuel processing module fluidly connected to the fuel cell stack. The fuel processing module may include a primary sorbent bed, a reserve sorbent bed, a valve configured to control fuel flow to the reserve sorbent bed, and a detector for detecting a breakthrough event in the primary sorbent bed. In some embodiments, the valve is configured to direct all or a majority of fuel flow through the primary sorbent bed, and upon detection of the breakthrough event, the valve is configured to direct all fuel flow or more fuel flow through the reserve sorbent bed.

Embodiment methods may include detecting undesirable constituents in a fuel cell system by detecting an undesirable constituent in a fuel flow into a fuel cell stack above a threshold level with at least one of a color change detector, an electrical resistance detector, and an artificial nose detector, and performing at least one of shutting off the fuel cell stack and directing at least a portion of the fuel flow through a different sorbent bed in response to detecting the undesirable constituent above the threshold level.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

FIG. 13 is a flow chart illustrating a method of detecting undesirable constituents in a fuel cell system.

FIG. 14 is a flow chart illustrating a method of detecting undesirable constituents in a fuel cell system.

DETAILED DESCRIPTION

Figure 1A:
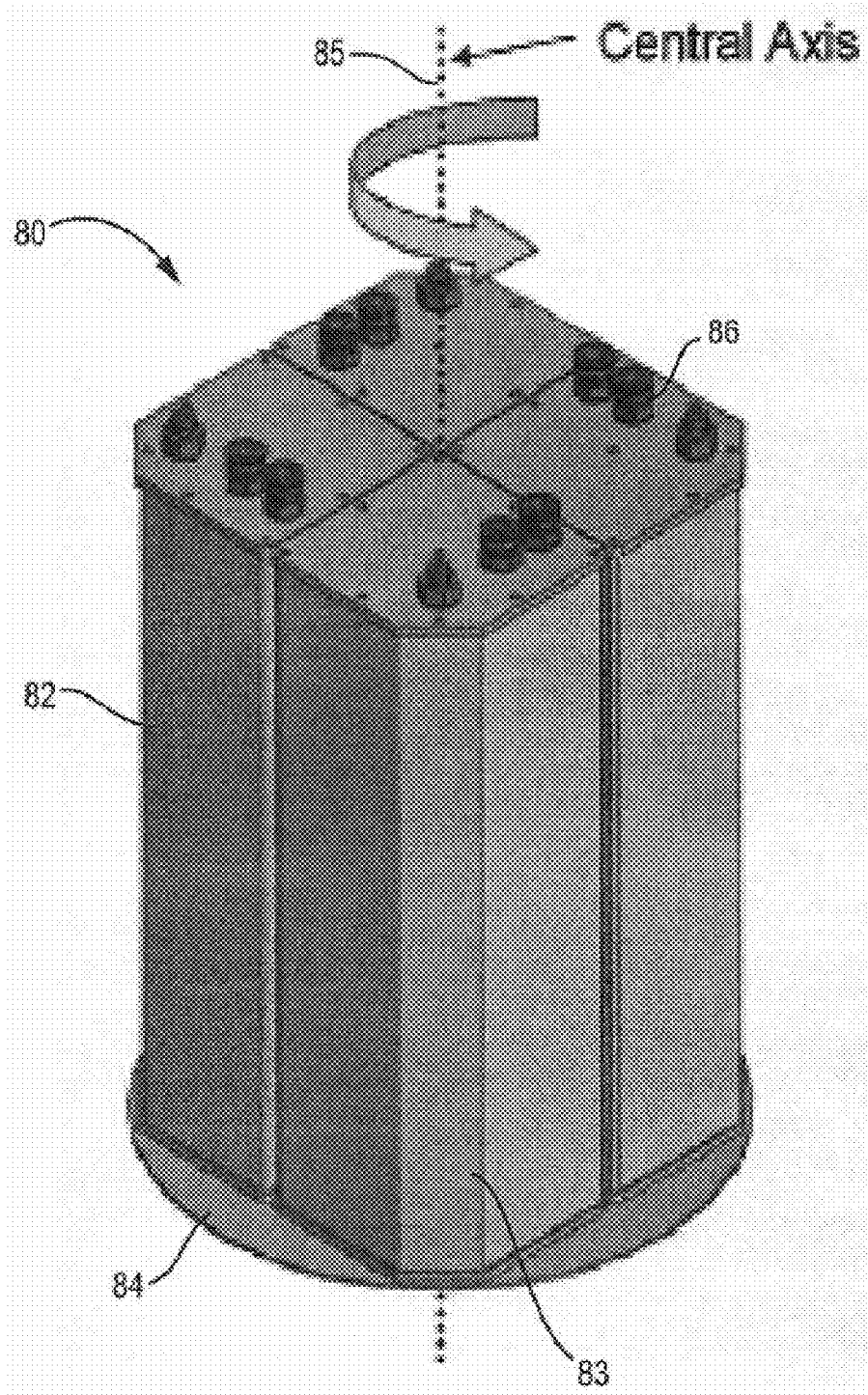
FIG. 1A illustrates an isometric view of a rotatable sorbent bed assembly for the fuel cell system according to an exemplary embodiment.
Figure 1E:
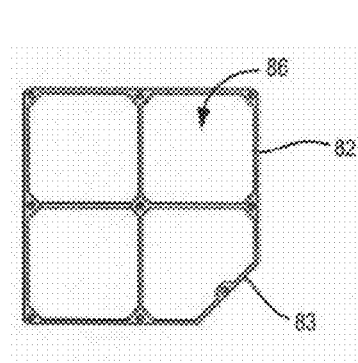
FIG. 1E illustrates a top view of the sorbent bed of FIG. 1B with the top removed to show internal chambers according to an exemplary embodiment.
Figure 1C:
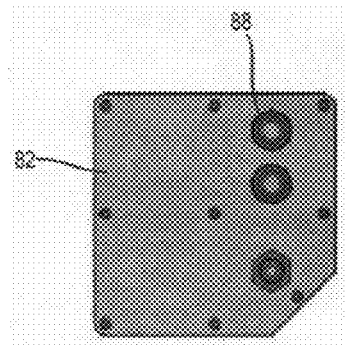
FIG. 1C illustrates a top view of the sorbent bed of FIG. 1B according to an exemplary embodiment.
Figure 1D:
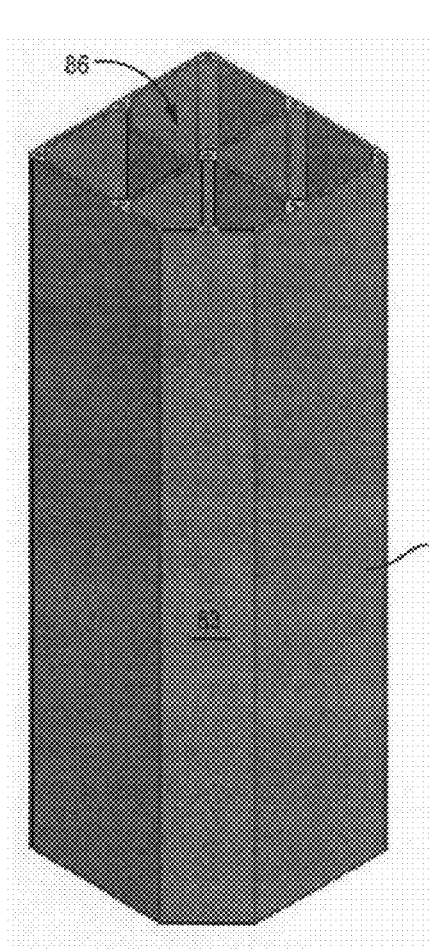
FIG. 1D illustrates an isometric view of the sorbent bed of FIG. 1B with the top removed to show internal chambers according to an exemplary embodiment.
Figure 1B:
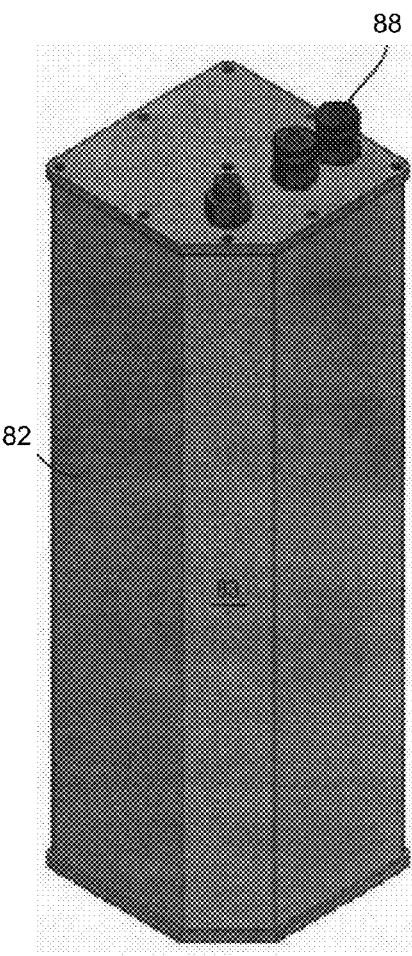
FIG. 1B illustrates an isometric view of a sorbent bed for the sorbent bed assembly of FIG. 1A according to an exemplary embodiment.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

"Fluidly connected" or variations thereof are defined herein as connected in a manner that allows the transfer of a fluid from one component to another. For example, a primary sorbent bed and a reserve sorbent bed may be fluidly connected in series. In this example, the primary sorbent bed and the reserve sorbent bed may have piping (i.e., conduits) such as stainless steel, carbon steel, or plastic (e.g., polyethylene) piping to connect the primary sorbent bed and the reserve sorbent bed in series so that a fluid (e.g., natural gas, biogas, etc.) may transfer from the primary sorbent bed to the reserve sorbent bed. It should be noted that the piping may be flexible, rigid, or some combination of the two. In another example, the primary sorbent bed may be fluidly connected to a fuel cell stack (e.g., to a power generation module in which a fuel cell stack is located). In this example, the fluid connection may be stainless steel tubing, which facilitates the transfer of the fuel (i.e., fluid) from the primary sorbent bed to the fuel cell stack (i.e., a power generation module). The term fluidly connected may also encompass other connection mechanisms such as flanges, quick connects, valves, detectors, and/or meters (e.g., flow meters) between the individual components. Direct fluid connection means that there are no other components between the two units (e.g., between a first primary sorbent bed and a second primary sorbent bed) except the conduit connecting the two units. Indirect fluid connection means that fluid may pass through intermediate components (e.g., valves, detectors, flow meters) as well as connecting two units with a conduit.

An sorbent bed assembly (e.g., one or more sorbent beds located in a fuel processing module) may have the ability to reduce a fuel cell stack's exposure to undesirable constituents by detecting the undesirable constituent downstream from a given sorbent bed, which indicates a breakthrough event (i.e., bed exhaustion). Once a breakthrough event is detected, a reserve capacity sorbent bed may be used to prevent the undesirable constituent from reaching the fuel cell stack (i.e., power generation module). Specifically, control systems may change the operation of the fuel cell system by altering fuel flow, utilizing a reserve sorbent bed, powering portions of the fuel cell system on/off, selecting different fuel sources, etc. Additionally, a detection system may enable detection of undesirable constituents such as siloxanes, moisture, oxygen, sulfur (including sulfur compounds such as organosulfur compounds), and other fuel cell stack poisons. Sending data representative of undesirable constituent types to a database may be used to create an undesirable constituent map. Process controls may access the undesirable constituent type data and the undesirable constituent map to alter operations such as fuel flow, fuel source selection, and power to various portions of the fuel cell system. These alterations to the fuel cell system operation may prevent or reduce the exposure of fuel cell stack to the undesirable constituents, thereby improving efficiency and the operational life of fuel cell stack.

The embodiments of the invention provide improvements for using sorbent beds (i.e., absorption and/or adsorption beds) in a fuel cell system such as a SOFC system. The present inventors discovered that in a fuel cell system, primary use sorbent beds for removal of undesirable constituents (e.g., sulfur) may become exhausted, sending sulfur into the fuel cell stack (i.e., power generation module), causing irreversible damage to the stack. Although primary use beds may be periodically replaced prior to exhaustion based on calendar estimations, changes in fuel sources or other variables may alter sorbent bed exhaustion. Degradation of fuel cell performance may indicate that a primary use sorbent bed is exhausted. Alternatively, undesirable constituent detectors downstream from an sorbent bed may also help determine when an sorbent bed is exhausted, indicating that the sorbent bed needs to be serviced, and thereby reducing a fuel cell stack's exposure to the undesirable constituents.

One embodiment of the present invention involves the use of a reserve sorbent bed to filter undesirable constituents such as sulfur (including sulfur compounds) when it is determined that the primary use bed is exhausted. The reserve sorbent bed may then replace the primary use bed. Alternatively, the reserve sorbent bed may supplement the primary use bed after determining the primary use bed is exhausted. Depending on the arrangement, the primary use bed may be replaced and the fuel cell system may maintain its operations (i.e., continue generating electricity without stoppage during the sorbent bed exchange) using the reserve sorbent bed. For fuel with high undesirable constituent content, a low-cost upstream sorbent bed may be periodically used to reduce the undesirable constituent content in the fuel prior to sending the fuel through the main sorbent bed assembly (i.e., fuel processing module) and the rest of the fuel cell system, thus prolonging the life of the main primary use beds and the fuel cell stack (i.e., power generation module).

Traditional alternatives use two sorbent beds connected in series. After a scheduled period or a determination that one sorbent bed is exhausted, both sorbent beds are replaced. This leads to under utilization of one or both sorbent beds and wasted cost in replacing them. Thus, detecting bed exhaustion may provide added cost benefits to a fuel cell system by fully using each sorbent bed in an sorbent bed assembly (i.e., fuel processing module).

Sorbent bed exhaustion may be detected based on degradation of the fuel cell stack (i.e., power generation module) performance. Detection of degradation of fuel cell stack performance may include comparing the amount of fuel used by the fuel cell stack with the electrical potential difference (voltage) output of the fuel cell stack and/or monitoring a stack performance characteristic, such as fuel utilization, output power, etc. If the voltage output for a fuel cell stack drops below a threshold value (e.g., at least a 5% decrease in voltage) for a given fuel flow rate, then the fuel cell stack may detect that there is significant degradation, likely due to the fuel cell stack receiving undesirable constituents present in the fuel stream. A separate detector, such as a color change detector, electrical resistance detector, or an artificial nose, may detect bed exhaustion or additional undesirable constituents not filtered by the sorbent beds. These types of detection mechanisms may signal (e.g., directly or via a central controller) valves to divert flow from an exhausted bed to a reserve sorbent bed, switch fuel sources, reduce fuel flow to the fuel cell stack, or stop fuel flow to the fuel cell stack to prevent damage to the fuel cell stack. Additionally, detectors, such as color change detectors, may send undesirable constituent data based on the color change to a color change database to create a color change map. Controls from the fuel cell system may alter the fuel cell system (e.g., divert fuel to a reverse sorbent bed, shut down the fuel cell stack, etc.) based on the undesirable constituent map and undesirable constituents currently detected.

A non-limiting example of an sorbent bed assembly (i.e., fuel processing module) suitable for the embodiments of the present invention is illustrated in FIG. 1. The sorbent bed assembly (i.e., fuel processing module) 80 may include four sorbent beds 82 each containing a material for gas purification such as desulfurization material, etc. While four sorbent beds are shown, the assembly may contain any suitable number of sorbent beds, such as two, three, or more than four (e.g., five to ten). In various embodiments, the sorbent bed assembly 80 is depicted with either two or four sorbent beds, for ease of illustration. The sorbent beds 82 may be arranged on a rotatable support pad 84 that rotates about a central axis 85. The rotatable pad 84 allows easy access and separate servicing of each sorbent bed 82 without disturbing the operation of the other sorbent beds 82.

The sorbent beds 82 are generally rectangular prismatic bodies with a beveled edge 83. The beveled edge 83 helps to properly orient the sorbent bed 82 on the rotatable pad 84. The beveled edge 83 further allows for better space utilization when rotating all four sorbent beds 82 together by eliminating a corner of the sorbent bed 82 that would otherwise extend beyond the rotatable pad 84 and interfere with the rotation of the sorbent bed assembly (i.e., fuel processing module) 80. Tall and narrow sorbent beds 82 allow for the sorbent bed assembly to be placed in a deep and narrow space such as a cabinet.

Referring to FIGS. 1B-1E, each of the sorbent beds 82 may have four internal channels 86 (e.g., subdivisions chambers, etc.), with the fuel passing through each of the channels 86 in the sorbent bed in fluid series. Thus, if all four sorbent beds 82 are connected in fluid series, the sorbent bed assembly 80 (i.e., fuel processing module) essentially has sixteen channels 86 in fluid series. On the other hand, two sorbent beds 82 connected in series as a set may be connected in parallel to another set of two sorbent beds 82. In this case, a set of eight channels in series is connected in parallel with another set of eight channels in series. Regardless, the sorbent bed 82 is a low cost design, which may be manufactured using extrusion methods. The relatively large length/diameter ratio of the channel 86 increases material efficiency. The geometry of the channels 86 causes a moderate pressure drop and relatively uniform flow of the fuel inlet stream. Bulk mixing occurs at four points in each sorbent bed 82, reducing edge effects and bypass.

The channels 86 may contain different compounds which are optimized to remove different constituents in the fuel stream. Additionally multiple beds 82 connected fluidly may contain different compounds from one another which are optimized to remove different constituents from the fuel stream.

All input and output (I/O) connections 88 for the sorbent beds 82 are provided on the same side (e.g., the top side) of the sorbent bed assembly (i.e., fuel processing module) 80.

The I/O connections 88 are swiveling leak-tight connections. Swiveling connections allows for the sorbent bed assembly 80 to continue operating as it rotates about the central axis 85.

Figure 2:
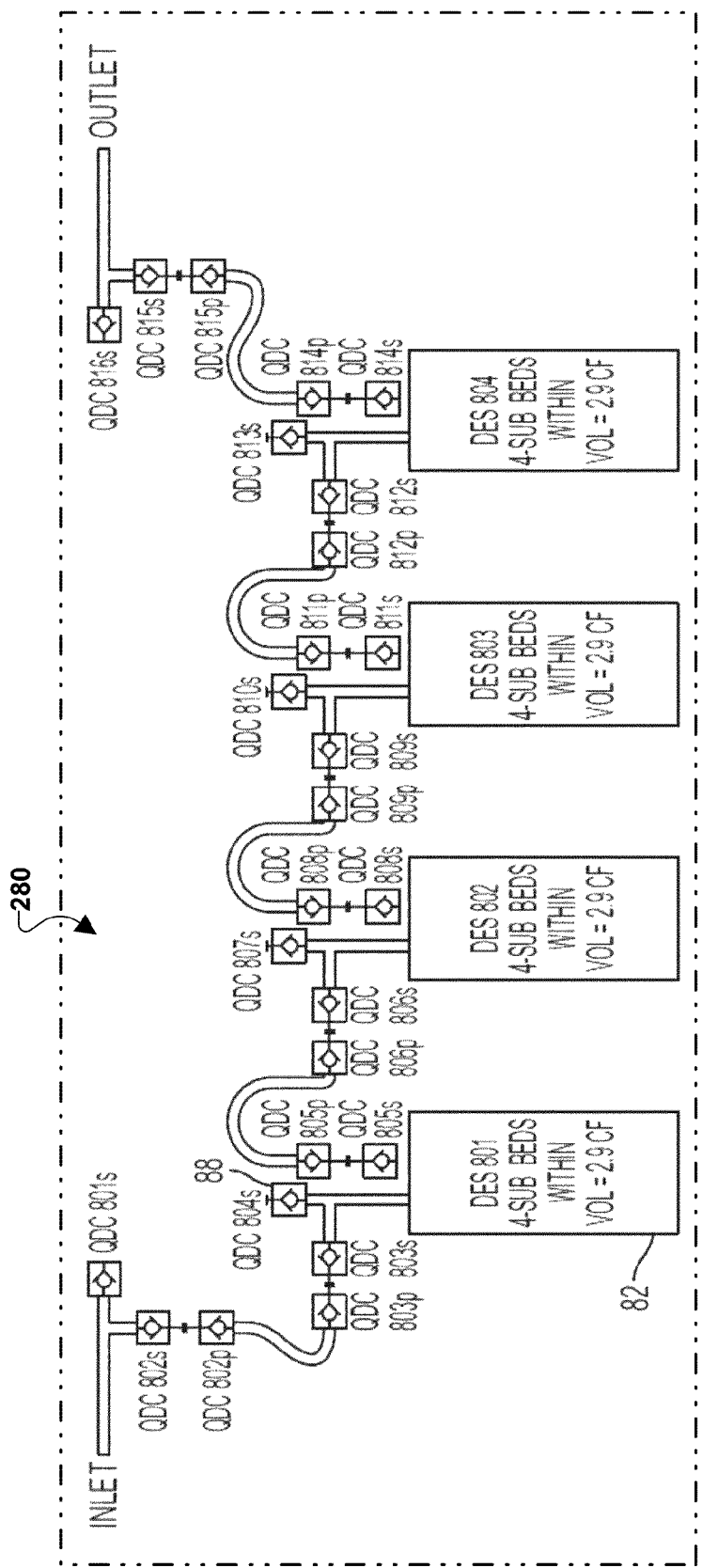
FIG. 2 schematically illustrates connections for the sorbent beds of the rotatable sorbent bed assembly of FIG. 1A according to an exemplary embodiment.

FIG. 2 illustrates an sorbent bed assembly (i.e., fuel processing module) 280 of four sulfur sorbent beds connected in series with I/O connections. The four sorbent beds DES 801, DES 802, DES 803 and DES 804 may have I/O connections 88, such as quick connects/disconnects 801s to 815s that allows a maintenance personnel to easily bypass and replace an sorbent bed.

In an embodiment, each of the sorbent beds 82 connected in series can absorb sulfur such as organosulfur compounds until the saturation level results in organosulfur compounds escaping the sorbent bed 82 without being absorbed. In normal operation of the sorbent bed assembly 280, the first three sorbent beds 82 connected in series are allowed to break through. Once a sulfur detector detects organosulfur compounds breaking through the third sorbent bed 82 in the series (e.g., DES 803), the first sorbent bed 82 (e.g., DES 801) is bypassed and then removed. The sorbent bed DES 801 may be bypassed by closing connection 803s-803p and connecting connection 802s to connection 805p. This way, the fuel inlet stream travels from the inlet directly through connection 802s-805p into the second sorbent bed DES 802 bypassing sorbent bed DES 801. Sorbent bed DES 801 is then removed from the assembly 280 to be refilled with fresh gas purification material. The sorbent beds 82 are rotated 90 degrees so that the sorbent bed 82/DES 802 that was originally second in the series is placed in the first position. Likewise, the sorbent bed 82/DES 802 formerly third in the series is moved into the second position and the sorbent bed 82/DES 804 formerly last in the series is moved to the third position. A new sorbent bed 82 is then placed in the fourth position. The new sorbent bed may be connected by having its inlet connected to connection 815p and its outlet connected to connection 815s while these two connections are bypassed. By doing so, each sorbent bed 82 is able to collect sulfur even after sulfur has broken through the third sorbent bed 82/DES 803.

Arranging the sorbent beds 82 on a rotatable pad 84 avoids confusion by making rotation procedure a constant. The use of four sorbent beds 82 allows connections between middle sorbent beds 82 in the cascade series to remain undisturbed while a spent sorbent bed 82 removed and a new sorbent bed 82 installed. Because of the arrangement of the sorbent beds 82 on the rotatable pad 84, all four sorbent beds 82 can be brought in close proximity to the front of a module housing container (e.g., to within 14 inches to meet UL requirements in the United States). The I/O connections 88 allow the inlet and the outlet plumbing to stay in the same place while the sorbent bed 82 change their place in order.

While the sorbent bed assembly (i.e., fuel processing module) 80 described above includes loose gas purification material in a generally rigid sorbent beds 82, in another exemplary embodiment, gas purification material may be pre-loaded into gas permeable bags. Then, the packaging of the gas purification material into the gas purification sorbent bed 82 is simplified via loading the bags into the sorbent bed structure—thereby eliminating the need to pour material into place. This further makes disassembly simpler because the bags may be quickly removed. Handles, ropes, or other features might be attached to the bags to aid in removal of bags of spent material from the sorbent beds 82. While a gas purification assembly is described above, any other sorbent bed assembly other than a gas purification assembly may include a rotatable support and a plurality of vessels arranged on the rotatable support, where each vessel contains a sorbent bed.

Sorbent Bed Connected in Series with a Reserve Sorbent Bed.

Saving a sorbent bed as a reserve sorbent bed may allow a maintenance personnel an extended period to replace the sorbent bed prior to sulfur or other undesirable constituents reaching the fuel cell stack (i.e. power generation module). During the normal (i.e., steady state) operation in the sorbent bed assembly (i.e., fuel processing module) 280, the last sorbent bed DES 804 may receive fuel with sulfur (e.g., organosulfur compounds) or other contents from the fuel, which may partially exhaust the sorbent bed's life. Thus, by taking sorbent bed/DES 804 offline during normal (i.e., steady state) operations, sorbent bed/DES 804 may be more effective in removing sulfur if brought online after sorbent beds DES 801-803 have become exhausted. A fresh sorbent bed/DES 804 may remove more sulfur content than a partially used sorbent bed, providing maintenance personnel more time while beds DES 801-803 are replaced/shifted, thus protecting the fuel cell stack from potential poisoning. In addition, during normal (i.e., steady state) operation, the fuel cell system will suffer from less pressure loss by having the fuel traveling through less sorbent beds (e.g., three instead of four).

Figure 3A:
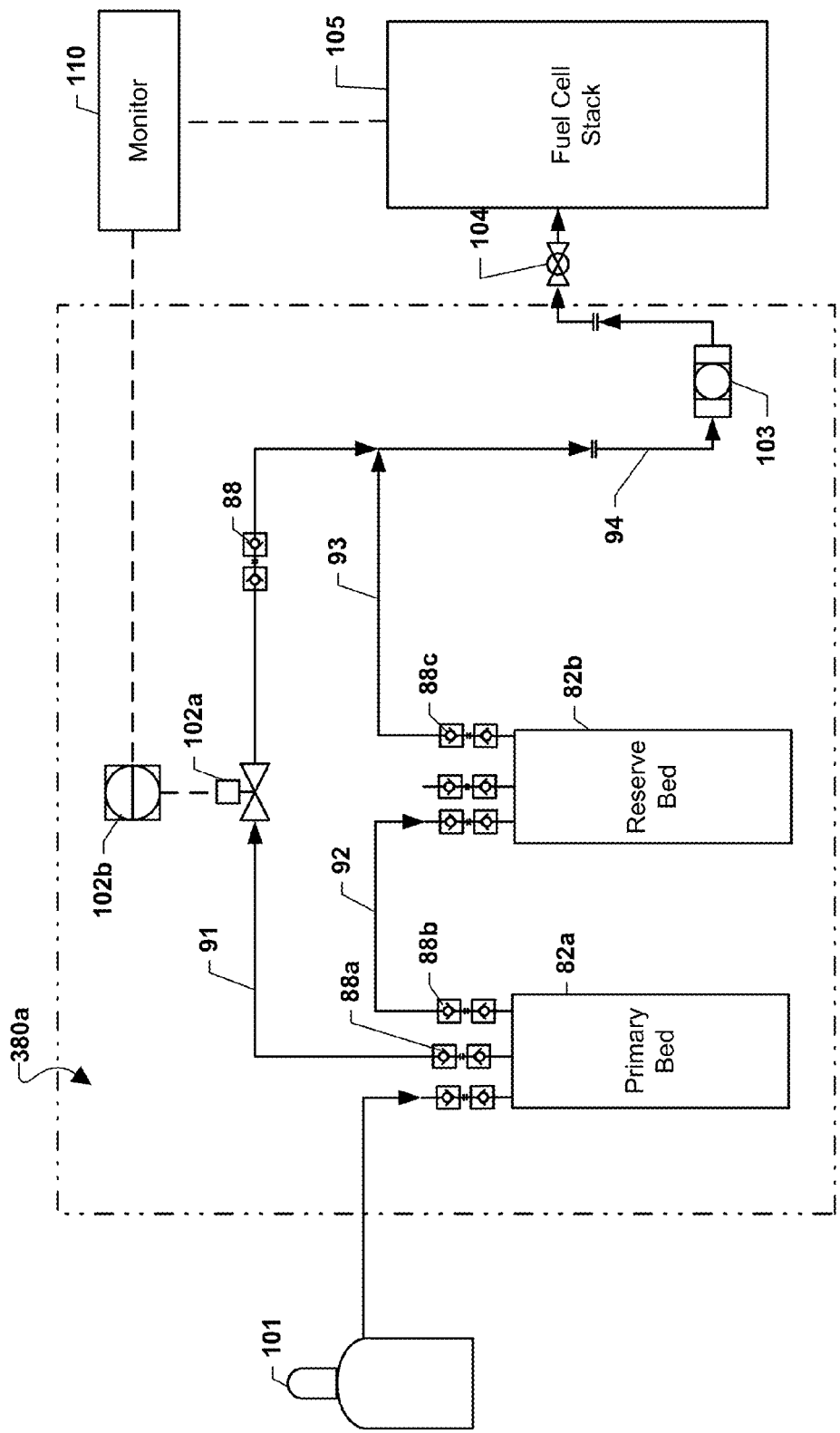
FIG. 3A illustrates a sorbent bed assembly with a primary sorbent bed and a reserve sorbent bed connected in series where the fuel cell stack's performance may dictate the use of a reserve sorbent bed.

FIGS. 3A-3D illustrate various configurations of sorbent bed assemblies (i.e., fuel processing module) 80 having beds connected in series. FIG. 3A illustrates a sorbent bed assembly 380a with two sorbent beds 82 fluidly connected to a fuel source 101 and a fuel cell stack (i.e., power generation module) 105. The fuel source 101 may be any source of fuel suitable for use with the sorbent bed assembly 380a and the fuel cell stack. Some examples include a holding tank, a pressurized tank, a gas cylinder, or a pipeline to a widely available fuel source, such as natural gas. The actual fuel source 101 may be natural gas, propane, methane, biogas, or any other fuel suitable for use with the fuel cell system.

One sorbent bed in the sorbent bed assembly 380a may be a primary use bed 82a and the other sorbent bed may be a reserve sorbent bed 82b. Fuel, such as natural gas, may flow from the fuel source 101 to the first primary sorbent bed 82a to remove undesirable constituents (e.g., sulfur). If valve 102a is open, fuel will flow through conduit 91 to conduit 94 and into the fuel cell stack 105 (i.e., power generation module), thereby bypassing connection 88b, conduit 92, the reserve sorbent bed 82b, and conduit 93. A monitor 110 may be a computer server or any other computing device electrically (or wirelessly) connected to a voltmeter, ammeter, and/or wattmeter and the fuel cell stack 105 as well as a flow meter connected to the fuel inlet of the fuel cell stack. The monitor 110 may monitor the performance of fuel cell stack 105 and if the monitor 110 determines that the fuel cell stack's performance has degraded due to poisoning (e.g., sulfur contamination of fuel cell anode electrodes), then it may send a signal to valve controller 102b, which actuates valve 102a in bypass conduit 91 to close. When valve 102a is closed, fuel that would normally bypass the reserve sorbent bed 82b via bypass conduit 91 travels from connection 88b via conduit 92 through the reserve sorbent bed 82b to capture sulfur material from the fuel stream. The fuel inlet stream then travels from sorbent bed 82b via connection 88c and conduits 93, 94 toward the fuel cell stack 105. The sorbent bed assembly 380a may have one or more I/O connections 88 on each sorbent bed 82, which allows the sorbent beds 82 to be replaced or serviced once spent. A particle filter 103 in the fuel inlet conduit 94 may remove any sorbent bed material (e.g., zeolite) caught in the fuel inlet stream to prevent the sorbent bed material from entering the fuel cell stack 105. A valve 104 may be used to isolate the sorbent bed assembly 380a from the fuel cell stack 105 for servicing the particle filter 103 (e.g., to remove a buildup of zeolite) or any other portion of the sorbent bed assembly. Additionally, valve 104 may serve as a failsafe to shut off fuel flow to the fuel cell stack if the concentration of any undesirable constituent is too high. Although FIG. 3A illustrates valve 104 as a manual valve, in an alternative configuration, it may be automatic.

Figure 3B:
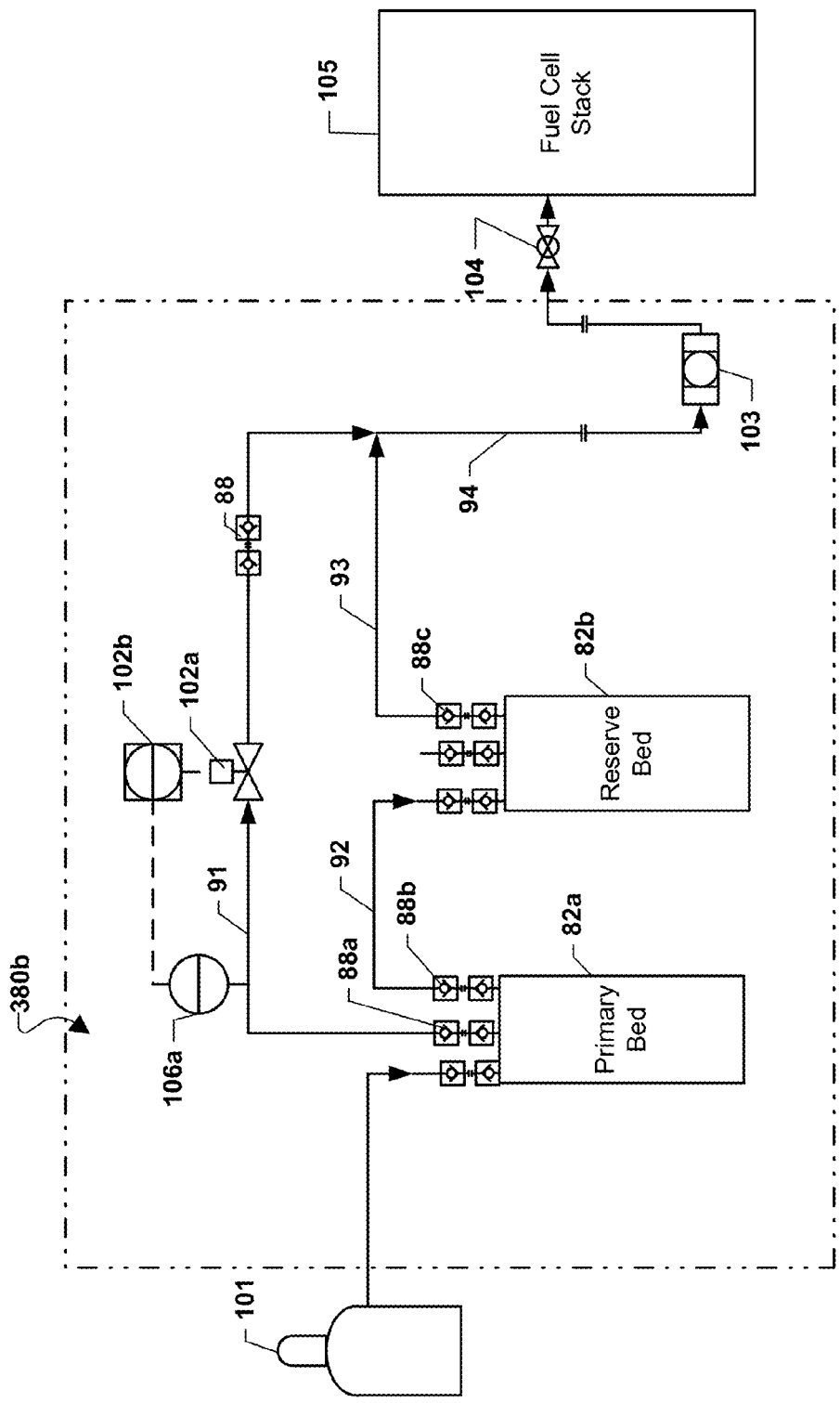
FIG. 3B illustrates a sorbent bed assembly with a primary sorbent bed and a reserve sorbent bed connected in series where a detector downstream from the primary sorbent bed may dictate the use of a reserve sorbent bed.

Although the fuel cell stack's performance may be used as an indicator of sorbent bed exhaustion or undesirable constituent detection, this involves exposing the fuel cell stack (i.e., power generation module) to unnecessary damage. Thus, using a detector may extend the life of the fuel cell stack and provide more accurate and real-time data to determine if an sorbent bed is exhausted and a breakthrough event has occurred. FIG. 3B illustrates an sorbent bed assembly 380b including a detector 106a that may be electrically connected (or wirelessly connected) to valve controller 102b in the bypass conduit 91 in sorbent bed assembly 380b. The detector 106a, such as a color change detector, a resistive detector, an artificial nose, or any other suitable detector type, may detect sulfur breakthrough of the fuel stream in the bypass conduit 91 downstream from the primary sorbent bed 82a and upstream from valve 102a. If the detector 106a detects an undesirable constituent (e.g., sulfur) at a threshold level then it may signal to the valve controller 102b to close valve 102a. This may prevent the undesirable constituent from entering the fuel cell stack 105 and send the fuel from the primary sorbent bed 82a to the reserve sorbent bed 82b via conduit 92. The detector 106a may indicate that the primary sorbent bed is exhausted or that the fuel stream has more sulfur content than the primary sorbent bed 82a can handle, thereby activating the reserve sorbent bed. The advantage to this embodiment is the fuel cell stack 105 is not the indicator of undesirable constituents in the fuel, reducing its exposure to them. The other elements of FIG. 3B are the same as in FIG. 3A and are not described for brevity.

Figure 3C:
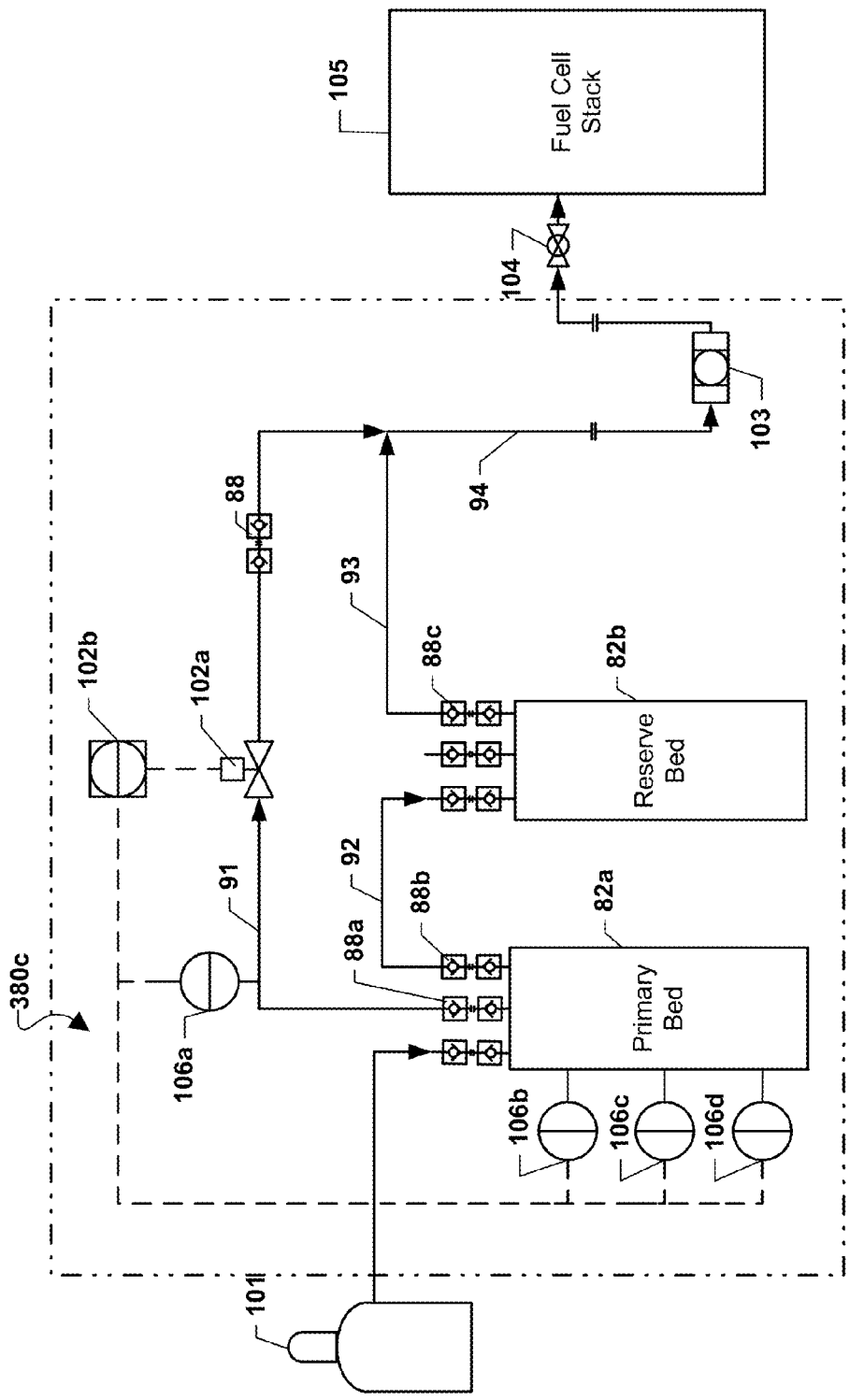
FIG. 3C illustrates a sorbent bed assembly with a primary sorbent bed and a reserve sorbent bed connected in series in which one or more detectors located on the primary sorbent bed may dictate the use of the reserve sorbent bed.

FIG. 3C is similar to FIGS. 3A and 3B except that FIG. 3C illustrates an sorbent bed assembly 380c with additional detectors 106b, 106c, and 106d located on/in the primary sorbent bed 82a as well as detector 106a located on the bypass conduit 91 downstream from the primary sorbent bed 82a. Although the sorbent bed assembly 380c illustrates four detectors 106a, 106b, 106c, and 106d, any number of detectors may be used for the sorbent bed assembly. For example, only one detector may be used in the sorbent bed assembly 380c, such as detector 106b located on/in the primary sorbent bed 82a. In another example, there may be one detector on the primary sorbent bed 82a and one detector in the bypass conduit 91 downstream from the primary sorbent bed 82a.

In a further example, there may be two or more detectors on/in the primary sorbent bed 82a with or without a detector 106a in the bypass conduit 91. The one or more detectors located on/in the primary sorbent bed may be electrically connected (or wirelessly connected) to the valve controller 102b such that if the detector(s) detect an undesirable constituent (e.g., sulfur) beyond a particular threshold level, then the detector(s) may signal to the valve controller 102b to close valve 102a. In an embodiment where the sorbent bed assembly 380c includes more than one detector, such as four detectors 106a, 106b, 106c, and 106d, each detector may detect different undesirable constituents. For example, detector 106a may detect sulfur to help determine a sulfur breakthrough event, while detector 106b may detect siloxanes, which may have an undesirable effect on the sorbent beds 82a and 82b and/or the fuel cell stack (i.e., power generation module) 105 resulting in less power generation from a given flow rate of fuel. Continuing this example, detectors 106c and 106d may each detect oxygen and excess water (or moisture), respectively, which may also degrade the performance of the fuel cell stack if either undesirable constituent reaches the fuel cell stack 105 via the fuel stream. In another embodiment where the sorbent bed assembly includes more than one detector, such as four detectors 106a, 106b, 106c, and 106d, two or more of those detectors may be redundant detectors for detecting the same undesirable constituent. A redundant detector may provide an additional measurement of a particular undesirable constituent (e.g., sulfur) allowing the sorbent bed assembly 380c to control the valve 102a based on the detection of more than one detector, thereby preventing a single defective detector from signaling or failing to signal the valve controller 102b to close valve 102a. For example, without a redundant detector, a single detector may be overdue for a calibration resulting in its lack of detection of sulfur in the fuel stream (or the primary sorbent bed). Instead of instructing the valve controller 102b to close valve 102a, as an accurate and properly calibrated detector would, it detects an acceptable amount of sulfur (e.g., less than the threshold level) in the fuel stream and does not instruct valve controller 102b to close valve 102a. Thus, fuel is never diverted through conduit 92 to the reserve sorbent bed 82b reducing the amount of sulfur in the fuel stream, which results in poisoning the fuel cell stack 105, once the sulfur enters the fuel cell stack through fuel inlet conduit 94. In an alternative example, where the sorbent bed assembly 380c includes an inaccurate detector and an accurate redundant detector, the accurate redundant detector may signal the valve controller 102b to close valve 102a bringing the reserve sorbent bed 82b online and preventing the fuel cell stack 105 from receiving an excess amount (or any amount) of sulfur.

In an alternative embodiment, the primary sorbent bed 82a may have at least two detectors 106b and 106c located on/in the primary sorbent bed, where each detector detects the same undesirable constituent (e.g., sulfur) but at different positions within the primary sorbent bed 82a. Each detector 106b, 106c may provide or contribute to an exhaustion status of the primary sorbent bed 82a providing information as to whether the primary sorbent bed 82a is partially exhausted or fully exhausted, which may be stored in a database or displayed on a computer screen. For example, the detector 106b may be located near the outlet of the primary sorbent bed, while detector 106c may be located in the middle of the primary sorbent bed. Detector 106c may detect that the primary sorbent bed is half exhausted and detector 106b may detect that the primary sorbent bed is fully exhausted and that it is time to switch to the reserve sorbent bed as well as replace the primary sorbent bed. The intermediate exhaustion status information may lead to lower operating cost of the fuel cell system resulting from decreasing unnecessary servicing of the primary sorbent bed due to more accurate predictions of an sorbent bed's exhaustion as well as lowering the need to maintain an inventory of replacement sorbent beds.

Figure 3D:
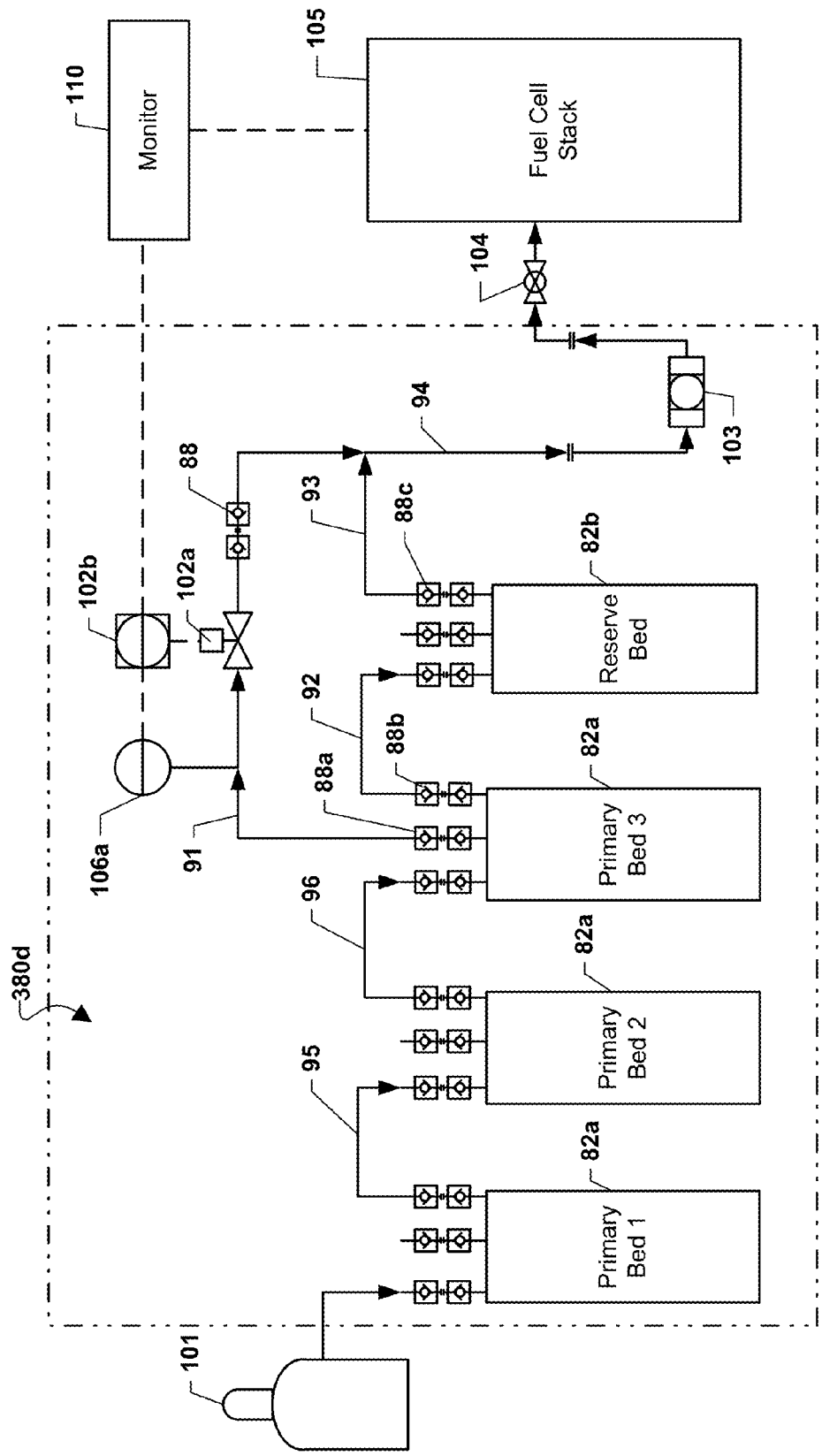
FIG. 3D illustrates a sorbent bed assembly with multiple sorbent beds connected in series in which a detector after the last primary sorbent bed and the performance of the fuel cell stack may dictate the use of the reserve sorbent bed.

Using more than two sorbent beds, such as four sorbent beds 82 arranged as shown in FIGS. 1A-1E and 2 may allow for longer life and more complete utilization of bed materials than two sorbent beds 82 shown in FIGS. 3A, 3B, and 3C. Combining the benefits of four sorbent beds with one reserve sorbent bed 82*b* may allow a service member more time to replace spent sorbent beds as well as provide less pressure loss across the fuel cell system during normal (i.e., steady state) operation. FIG. 3D illustrates a sorbent bed assembly 380*d* containing four sorbent beds, where three sorbent beds are primary sorbent beds 82*a* and one sorbent bed is a reserve sorbent bed 82*b*. While this embodiment shows that the detector 106*a* and monitor 110 of the fuel cell stack (i.e., power generation module) may provide instructions to the valve 102*a* to divert fuel flow from the bypass conduit 91 to the reserve sorbent bed 82*b*, only one of the detector 106*a* or the monitor 110 alone may provide the controlling instructions. In the sorbent bed assembly 360*d*, one detector 106*a* is placed downstream from the third primary sorbent bed 82*a* in bypass conduit 91. Once the detector 106 or the monitor 110 determines that a breakthrough event has occurred, valve 102*a* may be signaled to close diverting fuel normally bypassing reserve sorbent bed 82*b* into reserve sorbent bed 82*b*, thereby absorbing any undesirable constituent that is supposed to be filtered by the first three primary sorbent beds 82*a*.

In some embodiments, multiple detectors 106*a* may be used, which may be located earlier in the flow stream to judge the life expectancy of the entire set of primary sorbent beds 82*a* and perform various actions accordingly. Specifically, detectors 106*a* may be placed in any of conduits 95, 96, 92 and/or 93 downstream from each primary sorbent bed 82*a* and the reserve sorbent bed 82*b* to detect breakthrough events for each.

Figure 3E:
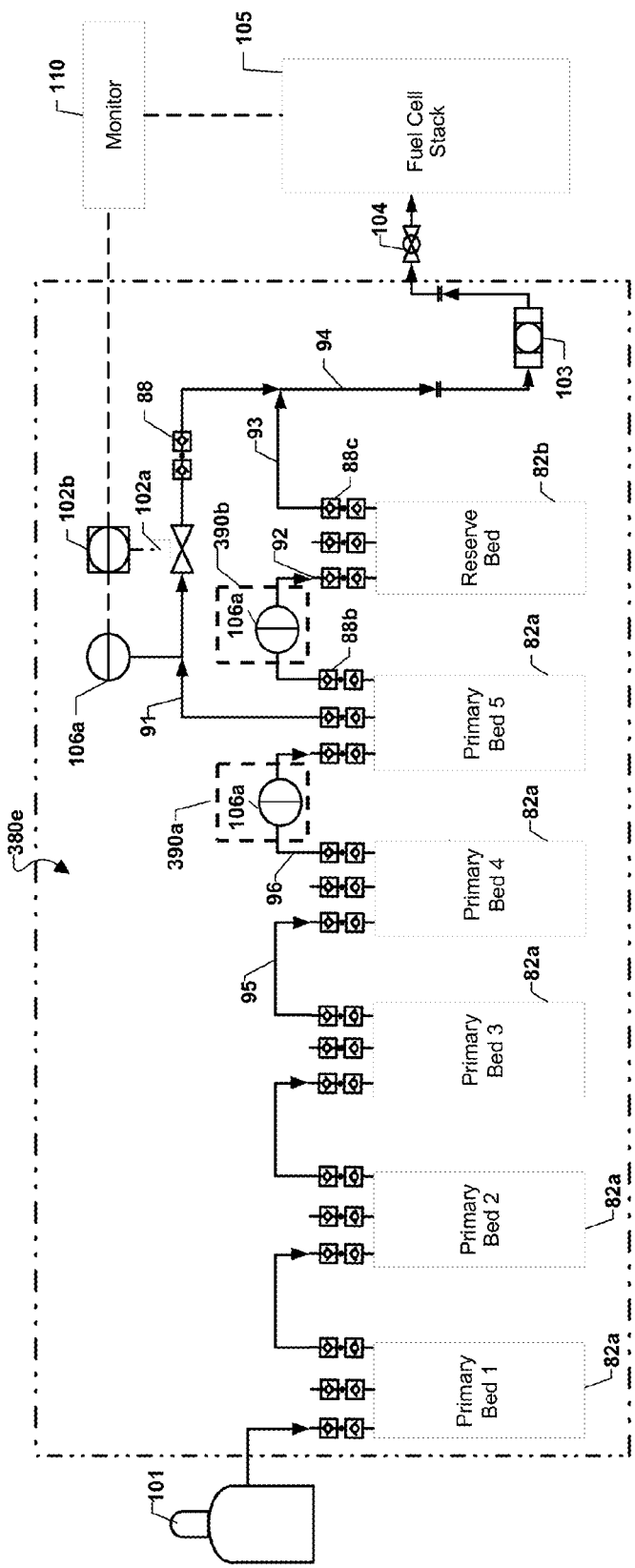
FIG. 3E illustrates a sorbent bed assembly with multiple sorbent beds connected in series in which detectors operating in subsystems may dictate the use of the reserve sorbent bed.

In some embodiments, multiple detectors 106*a* may be implemented in a sorbent bed assembly though multiple subsystems. FIG. 3E illustrates an example sorbent bed assembly 380*e* that operates using two subsystems, each containing a detector 106*a*. In the various embodiments, the sorbent bed assembly 380*e* may include six sorbent beds, where five sorbent beds are primary sorbent beds 82*a* and one sorbent bed is a reserve sorbent bed 82*b*. While this embodiment shows that the detectors 106*a* and monitor 110 of the fuel cell stack (i.e., power generation module) may provide instructions to the valve 102*a* to divert fuel flow from the bypass conduit 91 to the reserve sorbent bed 82*b*, only one of a detector 106*a* or the monitor 110 alone may provide the controlling instructions. In an embodiment, the sorbent bed assembly 380*e* may include a detector 106*a* located after the fourth primary sorbent bed 82*a* at conduit 96, which may operate in a first subsystem 390*a*. In an embodiment, the detector 106*a* of the first subsystem 390*a* may be configured to register a breakthrough of the first through fourth primary sorbent beds 82*a*. In normal operation, the first subsystem 390*a* may be enabled, and fuel from the fourth primary sorbent bed 82*a* may be directed through the fifth primary sorbent bed 82*a* and from the fifth primary sorbent bed 82*a* to the bypass conduit 91. Further, during normal operation, the second subsystem 390*b*, which may also contain a detector 106*a*, may be fluidly and/or electrically isolated/disabled (i.e., by closing isolation valves discussed below with respect to FIG. 3F). If a breakthrough from the first through fourth primary sorbent beds 82*a* is detected, in various embodiments the valve controller 102*b* may be signaled to close valve 102*a* in conduit 91, and to direct fuel from the fifth primary sorbent bed 82*a* into the reserve sorbent bed 82*b*. Further, detecting breakthrough from the first through fourth primary sorbent beds 82*a* may trigger activation of the second subsystem 390*b*, which may include another detector 106*a* downstream from the fifth primary sorbent bed 82*a* in conduit 92. Operation of the second subsystem 390*b* may include detection of a breakthrough from the first through fifth primary sorbent beds 82*a*. If a breakthrough from the first through fifth primary sorbent beds 82*a* is detected, an alert is generated to schedule a request for replacement of the primary sorbent beds 82*a*.

Figure 3F:
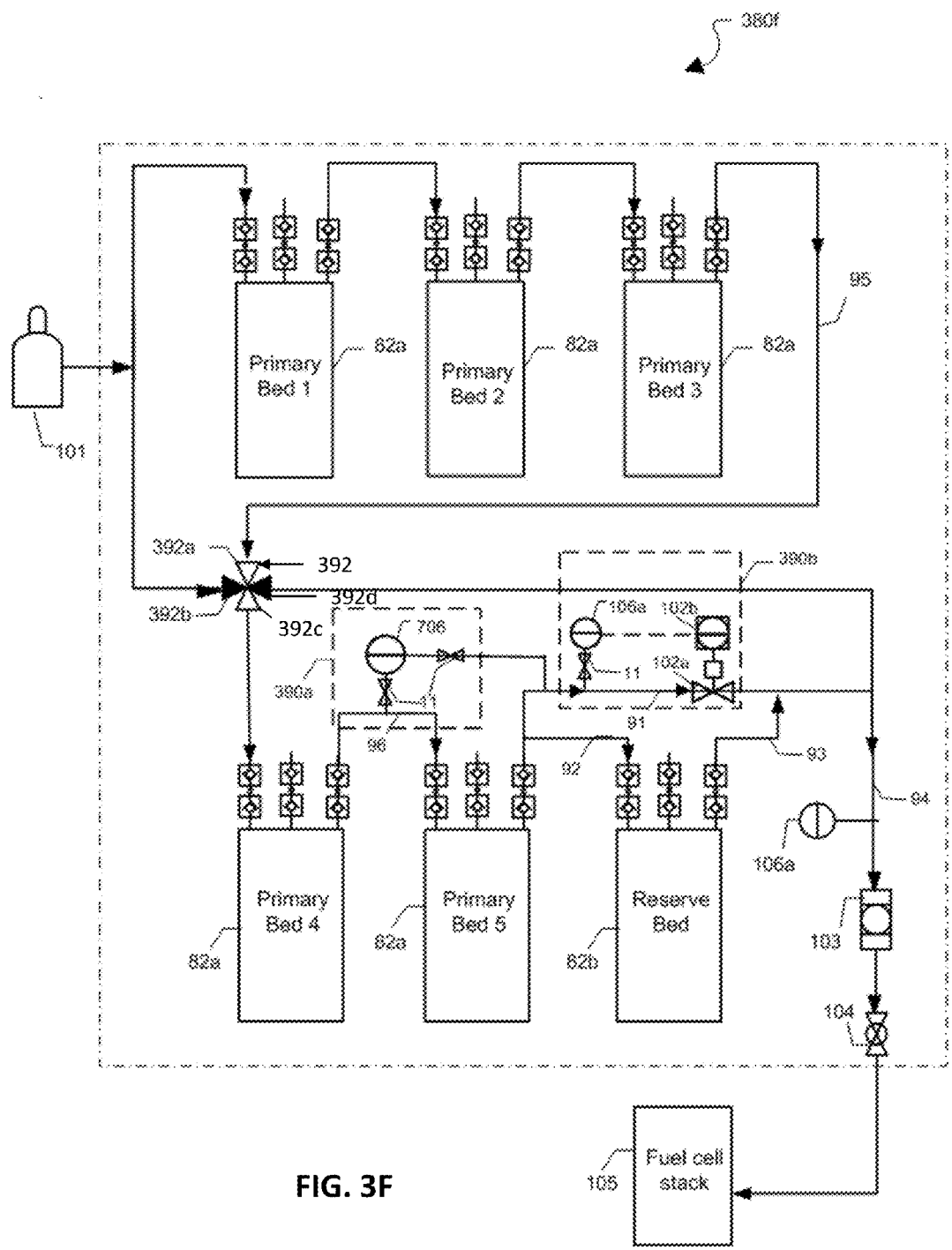
FIG. 3F illustrates a sorbent bed assembly with multiple sorbent beds connected in a configuration in which detectors operating in subsystems may dictate the use of the reserve sorbent bed.

FIG. 3F illustrates another example sorbent bed assembly 380*f* that operates using two subsystems, each containing a detector 106*a*. In the various embodiments, the sorbent bed assembly 380*f* may include six sorbent beds, where five sorbent beds are primary sorbent beds 82*a* and one sorbent bed is a reserve sorbent bed 82*b*. Similar to the sorbent bed assembly 380*e* discussed above with respect to FIG. 3E, the sorbent bed assembly 380*f* may include detectors located after the fourth and fifth primary sorbent beds 82*a*, which may operate in the first and second subsystems 390*a*, 390*b* respectively. In the sorbent bed assembly 380*f*, the first subsystem 390*a* may straddle outlet of the fourth primary sorbent bed 82*a* and the bypass conduit 91. The detector in the first subsystem 390*a* may be a slipstream detector 706. As discussed in further detail below with respect to FIG. 7, the slipstream detector 706 may receive a minority input fuel flow from one conduit (e.g., conduit 96), which is output into an adjoining conduit (e.g., bypass conduit 91) in parallel with the majority fuel flow (e.g., into the fifth primary sorbent bed 82*a*). Further, as shown in the sorbent bed assembly 380*f*, placement of a four-way valve 392 having inlets 392*a*, 392*b* may be used to divert fuel flow. The configuration of the sorbent beds, placement of the valve 102*a* to divert flow to the reserve sorbent bed 82*b*, and placement of an additional four-way valve 392 may provide additional configuration options, for example, isolating and/or bypassing the first through third sorbent beds, the fourth through sixth sorbent beds, the first subsystem 390*a*, the second subsystem 390*b*, etc.

For example, in normal operation, inlet 392*a* and outlet 392*c* of valve 392 may be open and inlet 392*b* and outlet 392*d* may be closed, causing fuel from the third primary sorbent bed 82*a* in conduit 95 to flow into fourth primary sorbent bed 82*a*. In another configuration (not shown) the four-way valve may allow the fuel flow to bypass the first through third primary sorbent beds 82*a* and initially enter the fourth primary sorbent bed 82*a* from the source 101 by opening inlet 392*b* and closing inlet 392*a* of valve 392. This allows the first through third beds to be serviced or replaced while the fuel cell stack 105 continues to operate to generate electricity. In another configuration (not shown), the fuel flow may occur as normal though the first three primary sorbent beds 82*a*, and the outlet flow from the third primary sorbent bed 82*a* in conduit 95 may bypass the fourth and fifth primary sorbent beds 82*a* and reserve sorbent bed 82*b* by closing outlet 392*c* and opening outlet 392*d*. This allows the fourth through sixth beds to be serviced or replaced while the fuel cell stack 105 continues to operate to generate electricity. If alarms and/or detectors in the sorbent bed assembly 380*f* indicate, for example, that breakthrough events have occurred in the first five beds, valve 102*a* may be closed thereby causing the fuel flow to pass through the reserve bed 82*b*. In the various embodiments, the detector 706 in the first subsystem 390*a* and a detector 106*a* in the second subsystem 390*b* may be configured with inlet/outlet isolation valves 11. Such valves 11 may be used to isolate/disable the detectors 706, 106*a* during various operating modes. For example, during normal operation, the detector 106*a* of the second subsystem 390*b* may be isolated/disabled by closing the associated valve 11, while during reserve operation (i.e., following a breakthrough event detected by the first subsystem 390a and closing of valve 102a) the detector 706 may be isolated/disabled by closing its associated isolation valves 11.

Some embodiment sorbent bed assemblies may include various sensor indicators. For example, a "watchdog" alarm may be included to check that a sensor is receiving power and communicating properly. Another example alarm may be a replacement alarm for sensing material in the one or more sensor. For example, the color of sensing materials may be checked against thresholds to identify whether the material of one or more sensor is spent and no longer functioning. In some embodiments, when a sensor is identified as containing spent sensing material, the control signaling may be configured to operate under a failsafe that assumes the presence of the applicable undesirable constituent(s). For example, in the sorbent bed assembly 380e discussed above with respect to FIG. 3E, if the detector 106a in the first subsystem 390a is identified as having spent sensing material, a replacement alarm may be triggered indicating replacement of the sensing material is needed for all detectors 106a. Further, following such identification of spent sensing material, the second subsystem 390b may be activated to monitor fuel flow through the first through fifth primary sorbent beds using at least one detector 106a as discussed above. If the detector 106a in the second subsystem 390b is identified as having spent sensing material, a replacement alarm may be triggered indicating replacement of the sensing material is needed for all detectors 106a. Following such identification of spent sensing material, operation of the reserve sorbent bed 82b may be activated as discussed above. Additional alarms that may exist include those indicating when a preset minimum and/or maximum lifetime expectancy has been reached for the sensing material in one or more detector 106a. Such lifetime expectancies may be preset estimations that are configured as estimations based on the materials used, type of undesirable constituent sensed, etc.

In various embodiments, the detectors 106a may be subjected to sensitivity testing in advance of use in order to ensure stability and avoid falsely tripping alarms. For example, a definite screening test may be performed to simultaneously gauge the effects of numerous factors on the detectors 106a used in a sorbent bed assembly.

In some embodiments, a system for a sorbent bed assembly may implement dynamic learning to improve its operation over time by monitoring and receiving instantaneous data and/or lifetime statistics. The instantaneous data may include, but are not limited to, flow rate and pressure estimates at each sorbent bed, and a cumulative gas flow across all sorbent beds. The lifetime statistics may include, but are not limited to, hours of operation for each sorbent bed (i.e., number hours in which the fuel flow of the bed is greater than zero), cumulative gas flow across all sorbent beds, and the last replacement date for each sorbent bed. These dynamic learning metrics may pertain to a sorbent bed 82 and/or to a detector 106. Further, the various embodiments may include learning metrics that are based on comparing metrics for a sorbent bed 82 with metrics for a detector 106. For example, the total fuel flow through a sorbent bed 82 may be compared to the total fuel flow through a detector 106.

Sorbent Bed Connected in Parallel with a Reserve Sorbent Bed.

Figure 4A:
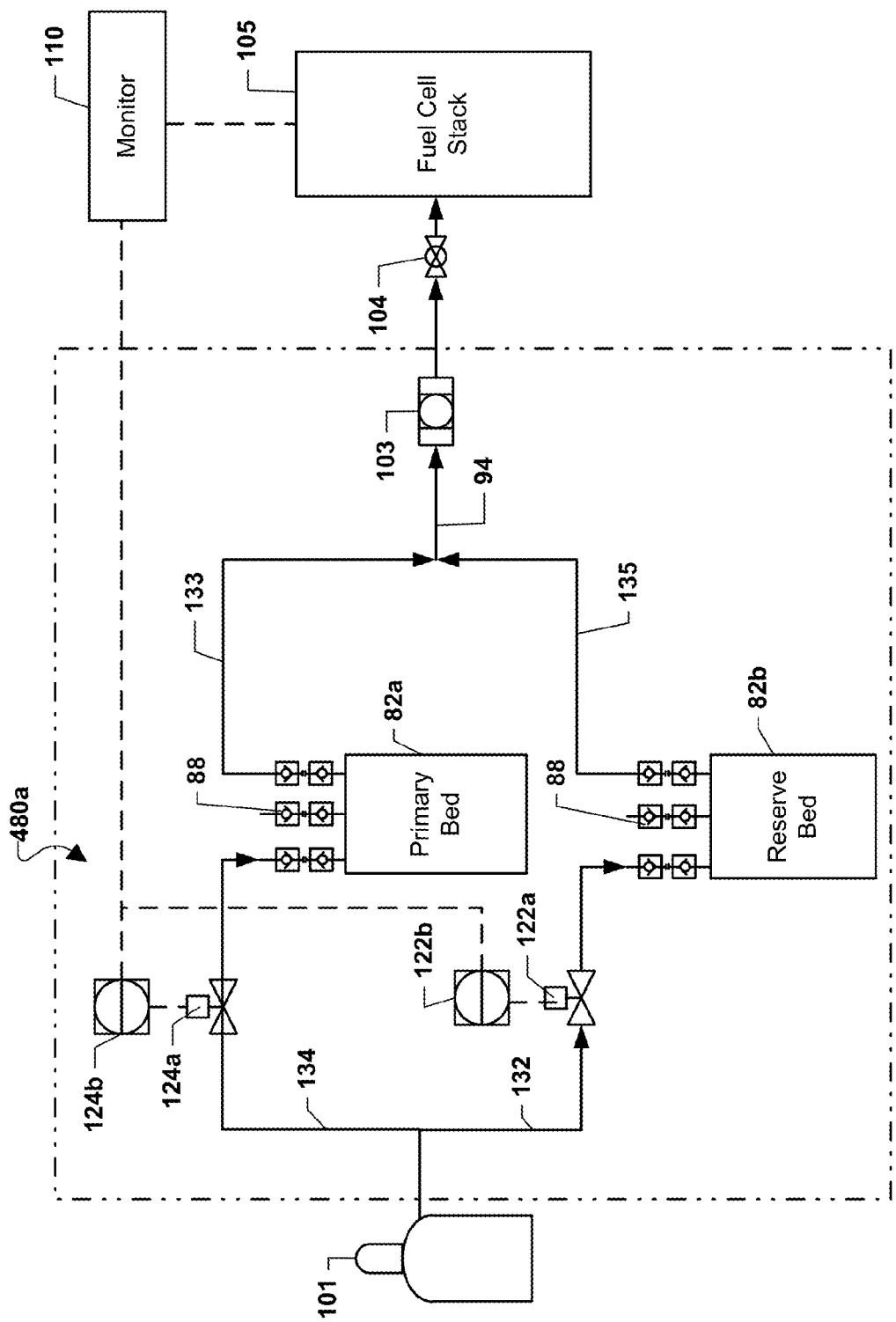
FIG. 4A illustrates a sorbent bed assembly with multiple sorbent beds connected in parallel in which a fuel cell stack's performance may dictate fuel flow to a reserve sorbent bed and a primary sorbent bed.

FIGS. 4A-4D illustrate another embodiment of sorbent bed assemblies (i.e., fuel processing module) with at least two sorbent beds connected in parallel. FIG. 4A illustrates a sorbent bed assembly 480a with one primary sorbent bed 82a and one reserve sorbent bed 82b fluidly connected in parallel. During normal (i.e., steady state) operation valve 124a in primary fuel inlet conduit 134 may remain open while valve 122a in reserve fuel inlet conduit 132 may remain closed forcing fuel from the fuel source 101 to travel only through the conduit 134 and primary sorbent bed 82a and into the fuel cell stack (i.e., power generation module) via conduits 133 and 94. Upon detection of a breakthrough event by a monitor 110 that detects a reduction in performance of the fuel cell stack 105, the monitor 110 may send a signal to valve controller 124b to close valve 124a and simultaneously send a signal to valve controller 122b to open valve 122a. This forces all fuel to flow through conduit 132 into the reserve sorbent bed 82b and from bed 82b via conduits 135 and 94 into the fuel cell stack 105. This allows the fuel cell system to continue to operate while primary sorbent bed 82a is serviced. By shutting fuel flow to the primary sorbent bed 82a, it is effectively isolated from the fuel cell system and may be easily serviced. If the monitor 110 detects another reduction in efficiency from the fuel cell stack 105 and the exhausted primary sorbent bed 82a has been replaced, then monitor 110 may signal valve 124a to open and valve 122a to close so fuel may flow through the replaced primary sorbent bed 82a and the reserve sorbent bed 82b may be serviced.

In an alternative embodiment, valves 122a and 124a may be flow control valves, and during normal (i.e., steady state) operation, both valves are opened. Valve 124a may be fully opened allowing a majority (greater than 50%, such as 60-95%) of fuel to flow through conduit 134 and the primary sorbent bed 82a, and valve 122a may be partially open allowing a minority (less than 50%, such as 5-40%) of fuel to flow through conduit 132 and the reserve sorbent bed 82b. Upon detection of reduced performance at the fuel cell stack (i.e., power generation module) 105, the monitor 110 may instruct controller 124b to close valve 124a and instruct controller 122b to fully open valve 122a. This forces all of the fuel to pass through conduit 132 and the reserve sorbent bed 82b prior to entering the fuel cell stack 105 via conduits 135 and 94. Since no fuel is traveling through the exhausted primary sorbent bed 82a, it may be replaced. Once the exhausted primary sorbent bed 82a is replaced, the valves 124a and 122a may adjust so that a minority of fuel flows through the replaced primary sorbent bed 82a acting as the reserve sorbent bed and the original reserve sorbent bed 82b may act as a primary sorbent bed until another breakthrough event occurs. This embodiment assembly 480a may allow full utilization of sorbent beds 82a, 82b and continued use of the fuel cell system, thereby reducing operational costs by minimizing early replacement of the sorbent beds and increase energy production of the fuel cell stack.

Figure 4B:
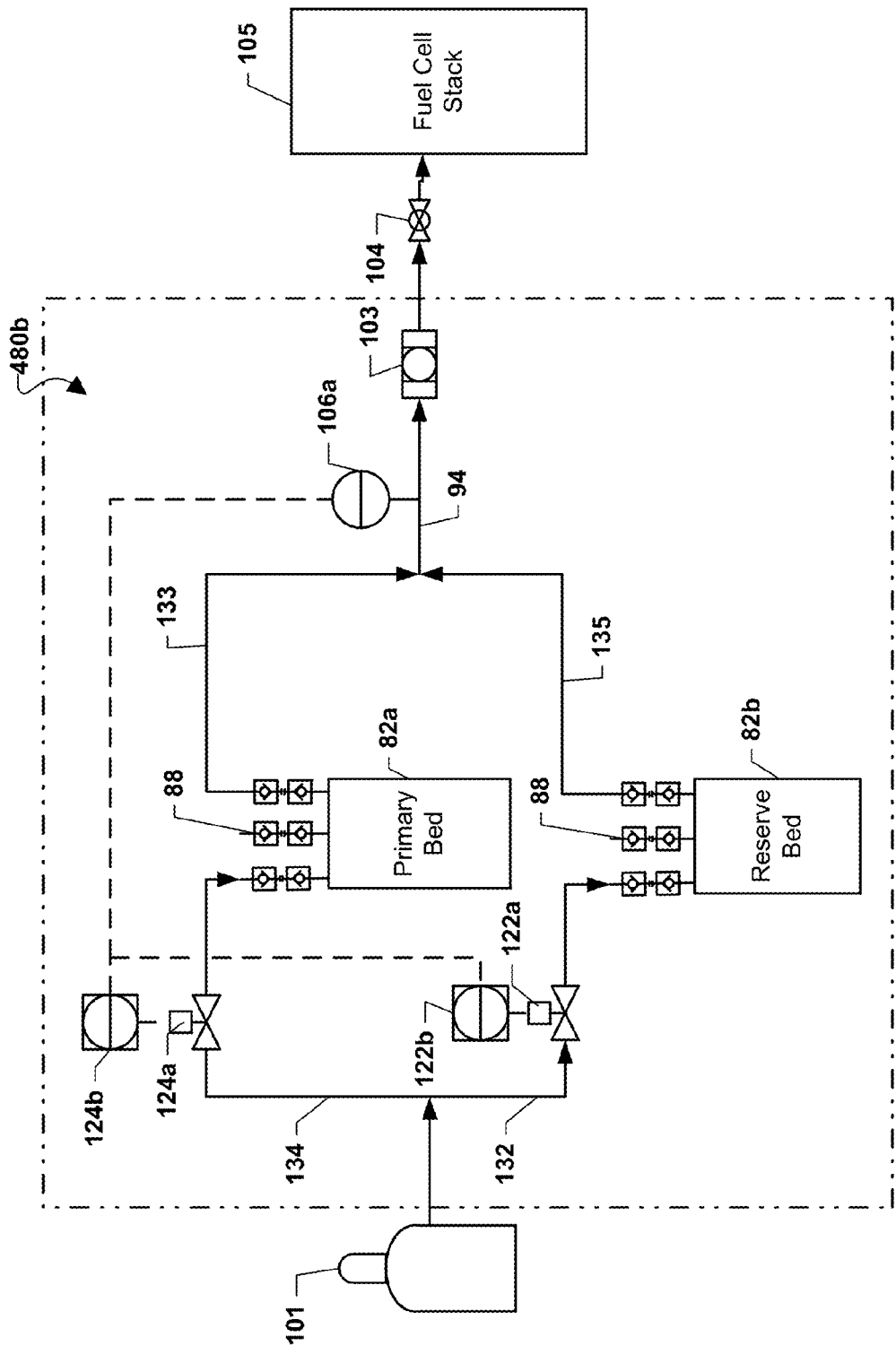
FIG. 4B illustrates a sorbent bed assembly with multiple sorbent beds connected in parallel in which a detector may dictate fuel flow to a reserve sorbent bed and a primary sorbent bed.

FIG. 4B illustrates another embodiment system 480b. In this system, a detector 106a may be electrically connected (or wirelessly connected) to valve controllers 122b, 124b in embodiment 480b. The detector 106a may be located on fuel inlet conduit 94 and may detect and analyze the presence of an undesirable constituent (e.g., sulfur) in the inlet stream of the fuel cell stack (i.e., power generation module). If detector 106a detects an undesirable constituent at a threshold level then it may signal to the valve controller 124b to close valve 124a. Simultaneously, the detector 106a may send a signal to valve controller 122b to open valve 122a such that all fuel flows through sorbent bed 82b. The advantage to sorbent bed assembly 480b over 480a is the fuel cell stack 105 is not the indicator of undesirable constituents in the fuel, reducing its exposure to them. Similar to system 380b, other elements in FIG. 4B are the same as in FIG. 4A and are not described for brevity.

Figure 4C:
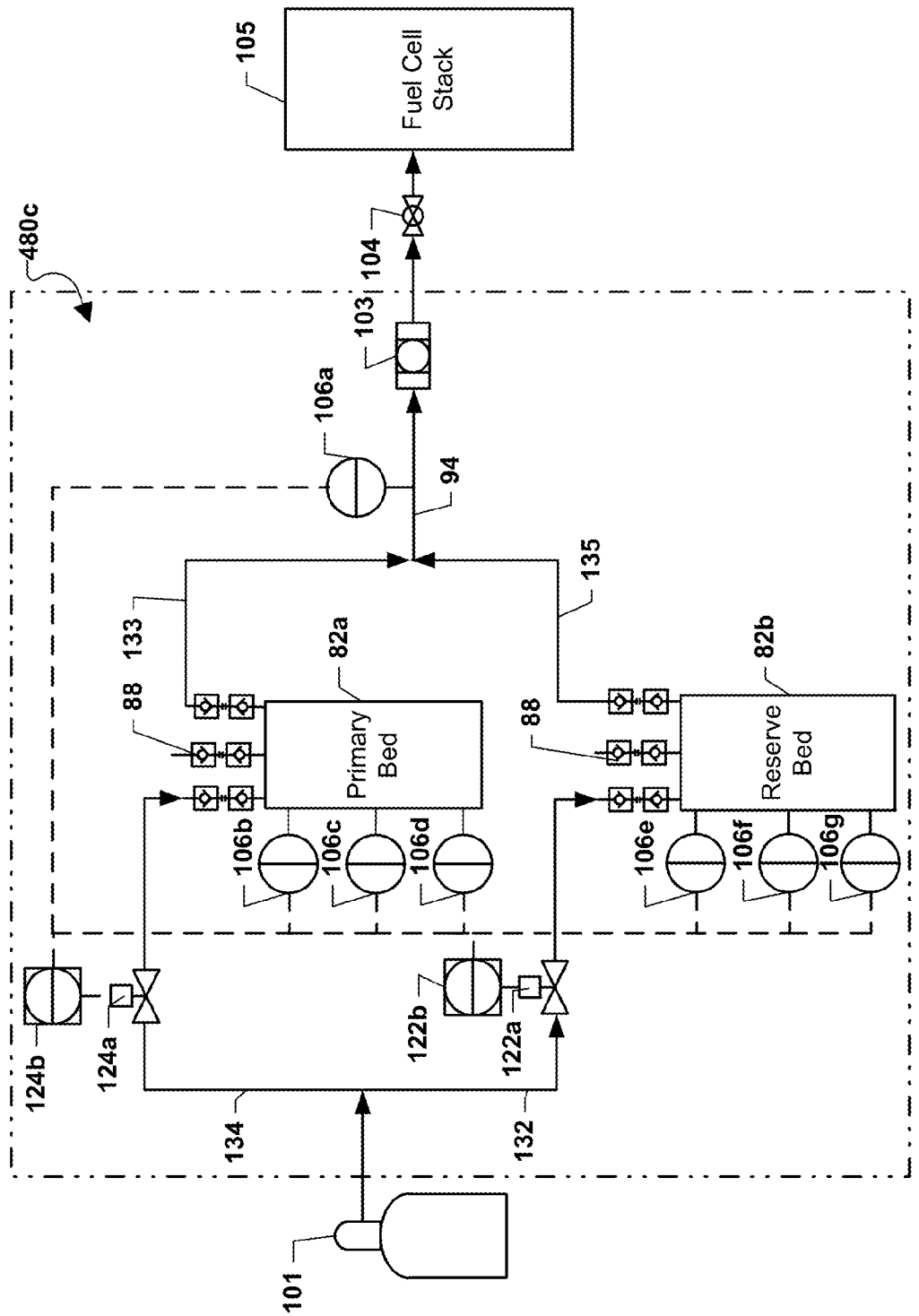
FIG. 4C illustrates a sorbent bed assembly similar to FIG. 4B, except that one or more detectors located on the primary sorbent bed and/or the reserve sorbent bed may dictate the use of either sorbent bed.

FIG. 4C is similar to FIGS. 4A and 4B except that FIG. 4C illustrates an sorbent bed assembly 480c with additional detectors 106b, 106c, and 106d located on/in the primary sorbent bed 82a and detectors 106e, 106f, and 106g located on/in the reserve sorbent bed 82b as well as detector 106a located on conduit 94 downstream from both the primary sorbent bed 82a and the reserve sorbent bed 82b. Although the sorbent bed assembly 480c shows seven detectors 106a-106g, any number of detectors may be used for the sorbent bed assembly. For example, only two detectors may be used in the sorbent bed assembly 480c, such as detector 106b located on the primary sorbent bed 82a and detector 106e located on the reserve sorbent bed 82b. In another example, the sorbent bed assembly may include only one detector on each of the sorbent beds 82a, 82b and one detector in conduit 94 downstream from the sorbent beds 82a, 82b.

In a further example, the sorbent bed assembly may include two or more detectors on/in each of the sorbent beds 82a, 82b with or without a detector 106a in conduit 94. Similar to detector 106a, the one or more detectors located on/in the sorbent beds 82a, 82b may be electrically connected (or wirelessly connected) to the valve controllers 124b, 122b such that when the detector(s) detect an undesirable constituent (e.g., sulfur) beyond a particular threshold level, then the detector(s) may signal to valve controllers 124b, 122b, to close their respective valves 124a, 122a. For example, in a steady state system where valve 122a is closed and valve 124a is open, all of the fuel from the fuel source 101 flows through conduit 134 to the primary sorbent bed 82a into conduits 133, 94, filter 103, valve 104, and the fuel cell stack (i.e., power generation module) 105.

If any of the detectors 106b-106d detect an undesirable constituent (e.g., sulfur) above a particular threshold level, then a detector, such as detector 106c, may instruct valve controller 124b to close valve 124a and instruct valve controller 122b to open valve 122a. As a result of this change, fuel flows from the fuel source 101 into conduit 132 before traveling through the reserve sorbent bed 82b. Similarly, instead of fully closing valve 124a in response to detecting an undesirable constituent, the detector may instruct the valve controller 124b to partially close valve 124a as well as instruct valve controller 122b to partially open (or fully open) valve 122a to cause a majority of the fuel to flow through the reserve sorbent bed 82b, while a minority of fuel still flows through the primary sorbent bed. In another example, in a steady state system where valve 122a is open and valve 124a is closed, all of the fuel from the fuel source 101 flows through conduit 132 to the reserve sorbent bed 82b into conduits 135, 94, filter 103, valve 104, and the fuel cell stack 105. If any of the detectors 106e-106g detects an undesirable constituent (e.g., sulfur) above a particular threshold level, then a detector such as detector 106f, may instruct valve controller 122b to close valve 122a and instruct valve controller 124b to open valve 124a. As a result of this change, fuel flows from the fuel source 101 into conduit 134 before traveling through the primary sorbent bed 82a. Similarly, instead of fully closing valve 122a in response to detecting an undesirable constituent, the detector may instruct the valve controller 122b to partially close valve 122a as well as instruct valve controller 124b to partially open (or fully open) valve 124a to cause a majority of the fuel to flow through the reserve sorbent bed 82b, while a minority of fuel still flows through the primary sorbent bed.

Similar to sorbent bed assembly 380c, the various embodiments of sorbent bed assembly 480c may include more than one detector, such as seven detectors 106a-106g, and may also include detectors for different undesirable constituents (e.g., water, oxygen, siloxanes, sulfur, etc.), redundant detectors for detecting the same undesirable constituents, and/or detectors to establish intermediary exhaustion status information of the sorbent beds. The advantages of an sorbent bed assembly 480c including different undesirable constituent detectors allows the system to adapt to multiple types of contaminants, by closing and/or opening valves in response to a particular undesirable contaminant being above an acceptable threshold level. The advantages of a sorbent bed assembly 480c including redundant undesirable constituents detectors allows the system to accept instructions from a properly working detector even when one detector of a redundant pair is not functioning properly (e.g., a valve having inaccurate detection, a lack of power, a damaged detector, etc.). The advantages of an sorbent bed assembly 480c including intermediate sorbent bed exhaustion detectors allows for lower overall operating costs due to accurate approximations of when an sorbent bed will be exhausted. The accurate sorbent bed exhaustion approximations leads to a decrease in unnecessary servicing of the sorbent bed (e.g., replacing a sorbent bed to early or too late) as well as a decreasing the need to maintain an inventory of replacement primary sorbent beds.

The intermediate exhaustion status information established by having one detector measuring undesirable constituents halfway through the sorbent beds 82a, 82b is a lower operating cost because the time a primary sorbent bed is exhausted may be more accurately predicted decreasing unnecessary servicing of the sorbent bed and lowering the need to maintain an inventory of replacement primary sorbent beds.

Figure 4D:
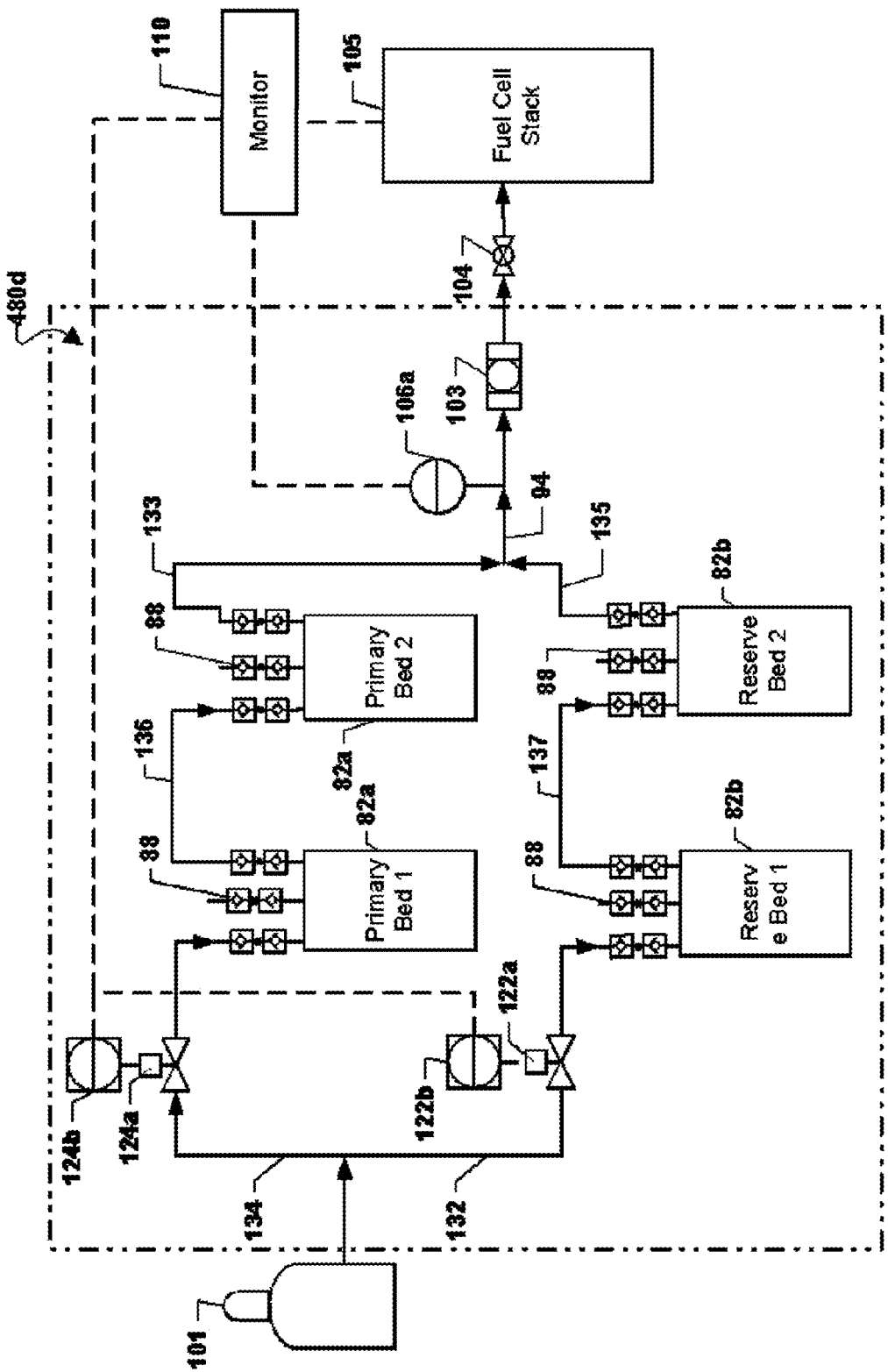
FIG. 4D illustrates a sorbent bed assembly with multiple sorbent beds connected in parallel and a detector and fuel cell performance may dictate fuel flow to the primary sorbent beds and the reserve sorbent beds.

As discussed above, using more than two sorbent beds, such as four sorbent beds 82 may allow for longer life and more complete utilization of bed materials than two sorbent beds as shown in FIGS. 4A, 4B, and 4C. Combining the use of a reserve sorbent bed along with four sorbent beds may allow for effective cost avoidance when servicing such a fuel cell system. FIG. 4D illustrates a sorbent bed assembly 480d containing four sorbent beds 82, where two primary sorbent beds 82a are fluidly connected in series by conduit 136 and two reserve sorbent beds 82b are fluidly connected in series by conduit 137. The two primary sorbent beds 82a are fluidly connected in parallel with the two reserve sorbent beds 82b. More than two primary sorbent beds 82a and/or more than two reserve sorbent beds 82b may be used. During normal (i.e., steady state) operation, valve 124a may remain open while valve 122a remains closed forcing fuel from fuel source 101 to travel only through primary sorbent beds 82a and into the fuel cell stack (i.e., power generation module) 105. Upon detection of a breakthrough event by the detector 106a, the detector 106a may signal controller 124b to close valve 124a and controller 122b to open valve 122a. Alternatively, monitor 110 may detect reduced performance of the fuel cell stack 105 and signal controller 124b to close valve 124a and controller 122b to open valve 122a. This will direct all of the fuel flow through reserve sorbent beds 82b isolating the primary sorbent beds 82a from the fuel cell system and allowing them to be replaced without disrupting the fuel cell stack's operation.

In an alternative embodiment, during normal (i.e., steady state) operation valve 122a may be partially opened. Valve 124a may be fully open (or partially open) allowing a majority of fuel to flow through primary sorbent beds 82a and valve 122a may be partially open allowing a minority of fuel to flow through reserve sorbent beds 82b. Upon detecting undesirable constituent breaking through primary sorbent beds 82a, detector 106a (or monitor 110) may instruct controller 124b to completely close valve 124a and instruct controller 122b to fully open valve 122a, thereby forcing all fuel to pass through reserve sorbent bed 82b prior to entering the fuel cell stack (i.e., power generation module) 105. Since no fuel is traveling through the exhausted primary sorbent beds 82a, they may be replaced. Once replaced, the valves 124a and 122a may adjust so that a minority of fuel flows through the new primary sorbent bed 82a acting as the reserve sorbent bed and the original reserve sorbent bed 82b may act as a primary sorbent bed until another breakthrough event. This may allow full utilization of sorbent beds materials and continued safe use of the fuel cell system.

While FIG. 4D illustrates that a detector 106a and a monitor 110 of the fuel cell stack (i.e., power generation module) may provide instructions to the valves 122a and 124a to divert flow to the reserve sorbent beds 82b, the detector 106a or the monitor alone may provide the controlling instructions. If using a detector 106a, it may be placed in conduit 94 downstream of (i.e., after) the junction of the reserve sorbent beds 82b and the primary sorbent bed 82a.

Upstream Reserve Sorbent Bed.

Figure 5:
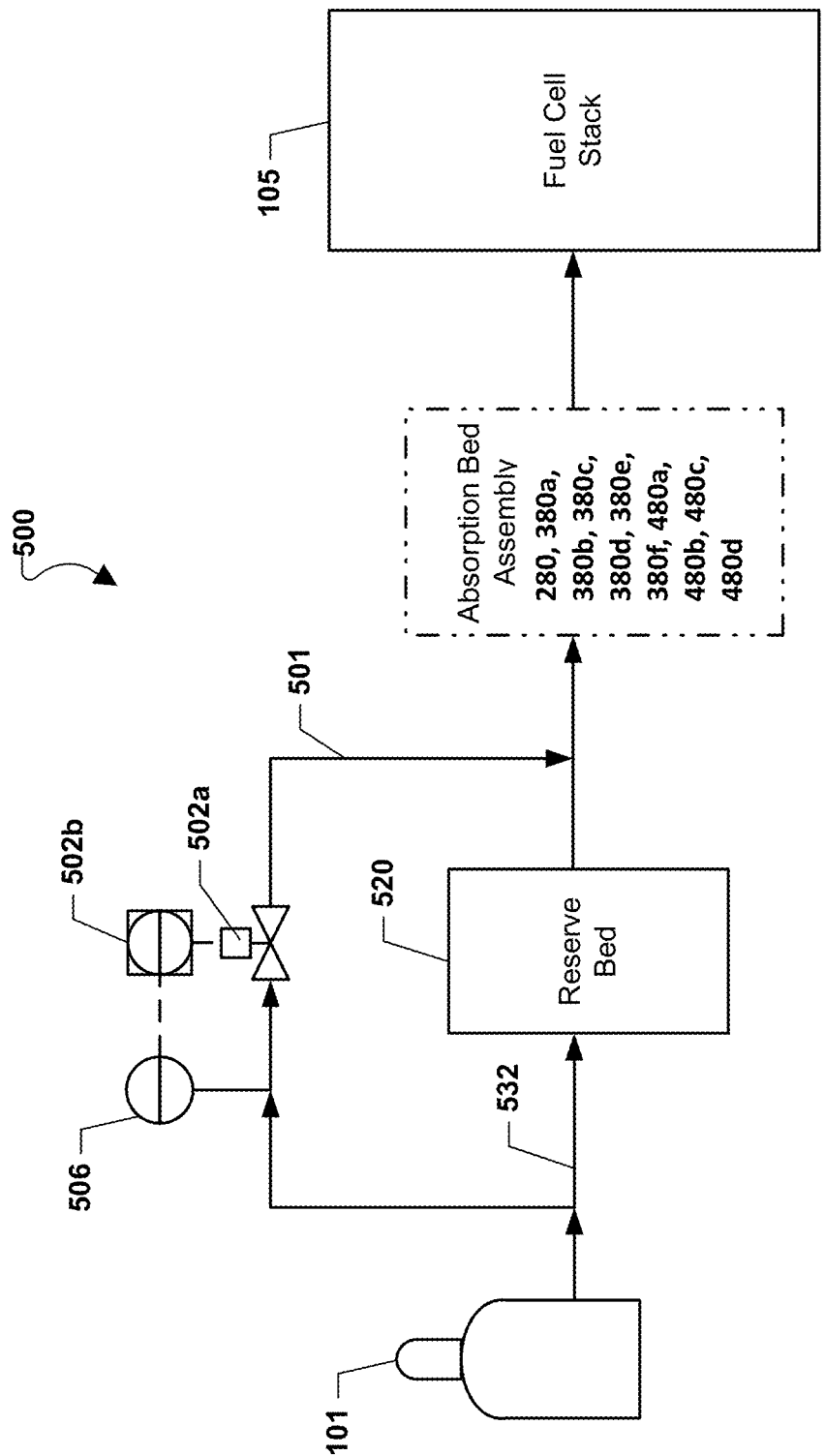
FIG. 5 illustrates an upstream sorbent bed with a bypass for fuel with high undesirable constituent content.

FIG. 5 illustrates an embodiment fuel cell system 500 that utilizes an upstream reserve sorbent bed 520 located outside of the modular fuel cell cabinets from the power generation module and the fuel processing module. The upstream reserve sorbent bed 520 may be used to remove excess sulfur (including sulfur compounds) from fuel provided from the fuel source 101 if the fuel is extremely high in sulfur content. Fuel may flow from the fuel source 101 through the upstream reserve sorbent bed 520 to remove almost all sulfur in a fuel, such as natural gas, prior to the fuel entering the sorbent bed assembly (i.e., fuel processing module), such as the assembly 280, 380a, 380b, 380c, 380d, 480a, 480b, 480c, or 480d described above. To comply with regulations regarding transporting deodorized natural gas (e.g., desulfurized natural gas) at a power generation site, fuel may periodically bypass the upstream reserve sorbent bed 520. For example, every ten minutes bypass valve 502a in bypass conduit 501 may open for thirty seconds to allow fuel to bypass the upstream reserve sorbent bed 520 via conduit 501. Thus, odorized natural gas is provided into the fuel cell system a fraction of the time. For example, odorized fuel bypasses reserve sorbent bed 520 0.1% to 10% of the time to allow nearby workers to determine if there is a natural gas leak in the system by smelling sulfur. Thus, upstream sorbent bed 520 removes most but not all sulfur to allow leak detection by smell.

In an alternative embodiment, the fuel cell system 500 may have a normal operating state (i.e., steady state) where the upstream reserve sorbent bed 520 is bypassed. Valve 502a is fully open and fluid dynamics cause fuel to flow around the reserve sorbent bed 520 via conduit 501 rather than through upstream reserve sorbent bed 520. Alternatively, an additional valve (not shown) in conduit 532 may prevent fuel from flowing into the reserve sorbent bed 520. Regardless, upstream detector 506 in conduit 501 may measure the amount of sulfur in the unpurified fuel stream. If the amount of sulfur meets a threshold level, indicating that fuel from fuel source 101 has a higher than desired undesirable constituent (e.g., sulfur) content, then the detector 506 may signal to controller 502b to close valve 502a forcing fuel through the upstream reserve sorbent bed 520.

Another alternative embodiment includes forcing fuel through the upstream sorbent bed 520 based on a detection of a breakthrough event by a monitor 110 or a detector 106 in the sorbent bed assembly (i.e., fuel processing module) 280, 380a, 380b, 380c, 380d, 480a, 480b, 480c, or 480d as described above. Either breakthrough detection method may signal controller 502b to close valve 502a to force fuel through the separate upstream reserve sorbent bed 520 prior to flowing through the sorbent bed assembly 280, 380a, 380b, 380c, 380d, 480a, 480b, 480c, or 480d.

As a further alternative, the upstream reserve sorbent bed 520 may be used to remove a different type of undesirable constituent than the sorbent bed assembly (i.e., fuel processing module) 280, 380a, 380b, 380c, 380d, 480a, 480b, 480c, or 480d. For example, the sorbent bed assembly 280, 380a, 380b, 380c, 380d, 480a, 480b, 480c, or 480d may remove sulfur while the upstream sorbent bed 520 may remove other undesirable constituents such as water (or moisture). Upstream detector 506 may measure water content in the fuel inlet stream from fuel source 101. During normal (i.e., steady state) operation, fuel from the fuel source 101 may bypass the upstream reserve sorbent bed 520 through open valve 502a and conduit 501. If the fuel stream from fuel source 101 comprises a threshold level of water, then a detector 506 located prior to valve 502a in conduit 501 may signal valve controller 502b to close valve 502a and divert fuel through the upstream reserve sorbent bed 520 to remove water. Subsequently, if moisture content is measured below a threshold value, then upstream detector 506 may signal valve 502a to open. Alternatively, the upstream reserve sorbent bed 520 may always be in use to remove water rather than only upon detection of a threshold level of water.

Fuel Source Switching.

Figure 6:
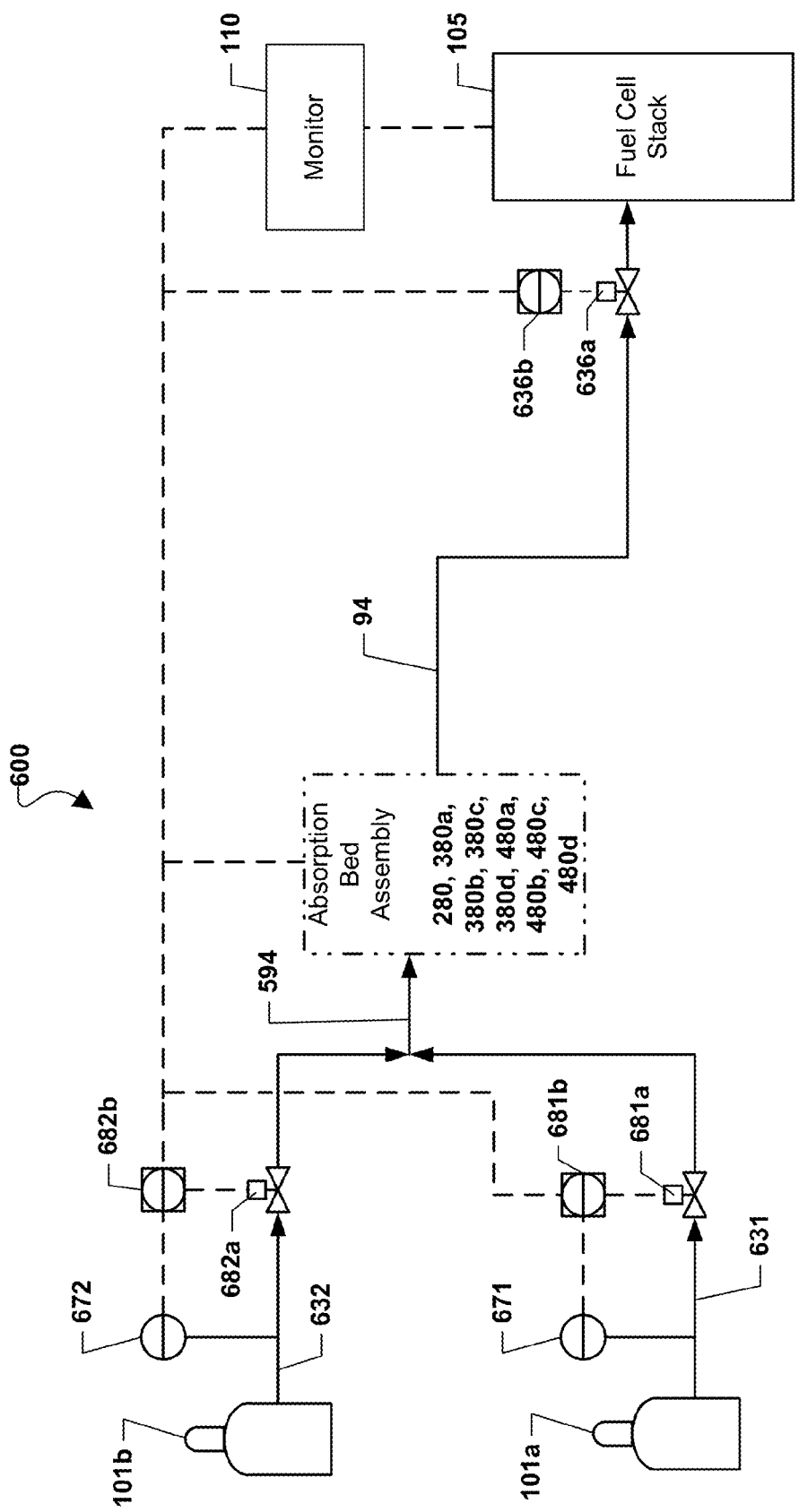
FIG. 6 illustrates a fuel cell system with undesirable constituent detectors and valves to select a fuel source based on feedback from the detectors.

FIG. 6 illustrates a fuel cell system 600 with multiple fuel sources (e.g., two or more sources) 101a, 101b. In the illustrated embodiments, each fuel source 101a, 101b may have respective associated detectors 672, 671, controllers 682b, 681b, and valves 682a, 681a. In a particular embodiment, the normal (i.e., steady state) operation may include using both fuel sources 101a, 101b by having valves 682a, 681a open. However, when one detector 672 or 671 detects an undesirable constituent, then the detector 672 or 671 signals to the respective valve controller 682b, 681b to close the respective valve 682a, 681a associated with the fuel source containing the high amounts of the undesirable constituent. For example, during normal (i.e., steady state) the fuel from both fuel sources 101a and 101b may flow through their respective conduits 631, 632, the common inlet conduit 594, sorbent bed assembly (i.e., fuel processing module) 280, 380a, 380b, 380c, 380d, 480a, 480b, 480c, or 480d described above, and through fuel inlet conduit 94 to the fuel cell stack (i.e., power generation module) 105. If detector 672 in conduit 632 detects that the undesirable constituent content from fuel source 101b is above a threshold level, it may signal controller 682b to close valve 682a to stop fuel from the fuel source 101b from entering the fuel cell stack 105. Thus, only fuel from fuel source 101a may be used in the fuel cell system 600. In another embodiment, if the performance of fuel cell stack 105 degrades below a threshold level, monitor 110 may send similar instructions to close valve 682a associated with fuel source 101a known (e.g., detected from detector 672) to have a high undesirable constituent content. As another failsafe, the fuel cell system 600 may include an automated valve 636a, which may turn on/off, or reduce the flow of fuel entering the fuel cell stack 105 when an undesirable constituent breakthrough event is detected.

In an alternative embodiment, the normal (i.e., steady state) operation may include using only one fuel source at a time until undesirable constituents are detected above a threshold level, and then switching to another fuel source. When the detector associated with the in use fuel source detects that the fuel stream contains an amount of undesirable constituents above a threshold level, the detector signals to close the valve associated with the in use fuel source while simultaneously signals to open the valve associated with the fuel source not in use. For example, during normal (e.g., steady state) operation only fuel from fuel source 101*a* may be used with the sorbent bed assembly (i.e., fuel processing module) 280, 380*a*, 380*b*, 380*c*, 380*d*, 480*a*, 480*b*, 480*c*, or 480*d* and the fuel cell stack (i.e., power generation module) 105. Detector 671 may detect particular undesirable constituents and concentrations of undesirable constituents in fuel from fuel source 101*a*. If a detector 106*a*-106*g* from sorbent bed assembly 280, 380*a*, 380*b*, 380*c*, 380*d*, 480*a*, 480*b*, 480*c*, or 480*d* detects a breakthrough event or monitor 110 detects the fuel cell stack 105 is suffering degradation of performance based on a undesirable constituent associated with fuel source 101*a*, then valve 681*a* may be signaled to close and valve 682*a* may be signaled to open. Thus, the fuel cell system 600 and the corresponding sorbent bed assembly 280, 380*a*, 380*b*, 380*c*, 380*d*, 480*a*, 480*b*, 480*c*, or 480*d* and fuel cell stack 105 only receives fuel from fuel source 101*b*, thereby switching fuel sources.

In an alternative embodiment, any or all of the detectors 672, 671, valves 682*a*, 681*a* and controllers 682*b*, 681*b*, 636*b* may be a part of the sorbent bed assembly 280, 380*a*, 380*b*, 380*c*, 380*d*, 480*a*, 480*b*, 480*c*, or 480*d*. The sorbent bed assembly 280, 380*a*, 380*b*, 380*c*, 380*d*, 480*a*, 480*b*, 480*c*, or 480*d* would be able to select particular fuel sources or change the fuel flow to the fuel cell stack (i.e., power generation module) 105 based upon the needs of the system 600.

Slipstream Detectors.

Figure 7:
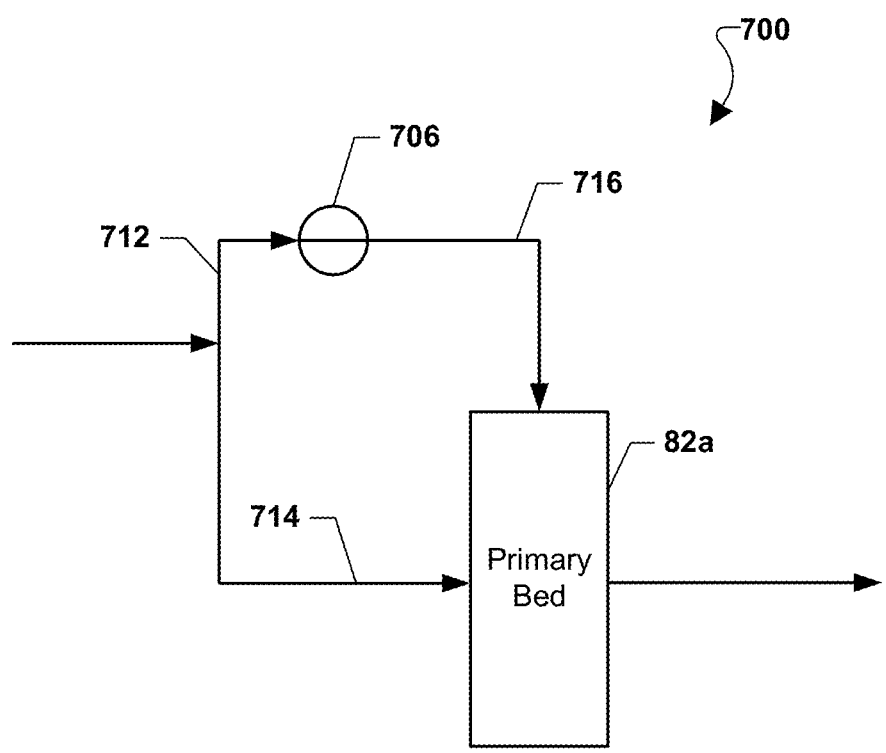
FIG. 7 illustrates a slipstream detector for use in the various sorbent bed assemblies.

FIG. 7 illustrates a detector 706 that receives fuel from conduit 712 and returns it into the primary sorbent bed 82*a* through a slipstream conduit 716. Although each detector in FIGS. 3B-3F and 4B-4D illustrates connecting in a t-joint fashion with its adjoining conduit or sorbent bed, the detectors illustrated and described with respect to these embodiments may utilize slipstreams similar to the one illustrated in FIG. 7. A slipstream detector 706 receives a minority fuel flow in parallel with the majority fuel flow in an adjoining conduit. In an embodiment, a minority of fuel may flow through conduit 712 into slipstream detector 706 and into the primary sorbent bed 82*a*. Simultaneously, a majority of fuel flows through conduit 714 and into the primary sorbent bed without traveling through the slipstream detector 706. As shown in FIG. 7, the slipstream detector 706 detects undesirable constituents upstream from the sorbent bed. The slipstream detector may detect the same undesirable constituent that the primary sorbent bed removes (e.g., sulfur), and may be used to switch fuel sources 101*a* and/or 101*b* as described above with respect to FIG. 6. Alternatively, the slip stream detector 706 may detect a different undesirable constituent than one that the primary sorbent bed removes. For example, if the primary sorbent bed removes sulfur, then the slipstream detector 706, located upstream from the primary sorbent bed detects another undesirable constituent, such as a siloxane.

In another embodiment, the slipstream detector 706 may be downstream from another sorbent bed (not shown). For example, a slipstream detector 706 may be located on conduit 95 in FIG. 3D, which is downstream of first primary sorbent bed 82*a* and upstream from the second primary sorbent bed 82*a*. In this example, the slipstream detector 706 may detect the same undesirable constituent (e.g., sulfur) that the first and second primary sorbent bed 82*a* remove providing a valuable detection of the undesirable content present downstream of the first primary sorbent bed. The detection downstream of the first primary sorbent bed may indicate a breakthrough event of the first primary sorbent bed and its need to be replaced. Additionally, the detection of breakthrough at an early sorbent bed may send a signal for the reserve sorbent bed 82*b* to be activated.

In another example, the slipstream detector 706 may be located on conduit 136 in FIG. 4D, downstream from the first primary sorbent bed 82*a* and upstream from the second primary sorbent bed 82*a*. Additionally, the slipstream detector 706 may be placed in conduit 137 in FIG. 4D, between the first and second reserve sorbent beds 82*b*. In either conduit 136 or conduit 137, the slipstream detector 706 may detect the same undesirable constituent (e.g., sulfur) that the first and second sorbent bed removes providing a valuable detection of the undesirable content present downstream of the first sorbent bed. The detection downstream of the first sorbent bed 82*a*, 82*b* may indicate a breakthrough event of the first sorbent bed 82*a*, 82*b* and its need to be replaced.

This slipstream detector may be connected across a feature in the main flow path such as a sorbent bed or a valve, such that the pressure drop created by that flow feature would drive flow through the slipstream detector.

This slipstream detector may employ valve(s) located on conduit 712 and/or conduit 716 to shut off flow to the detector. These valves would facilitate replacement of the sensor during system operation in the case that the color changing cartridge or the sensor are non-functional. Additionally the use of valves on the sensor's flow plumbing would allow for the ability to preserve the finite life of a color changing cartridge. An example is in an embodiment such as the system 380*c*. The use of valves on the inlet and/or outlets of the sensors 106 would allow sensor 106*d*, which is further in the flow path to be closed until some criteria is met, such as sensor 106*b* witnessing the breakthrough of undesirable constituents.

Detector and Database Map.

Figure 8A:
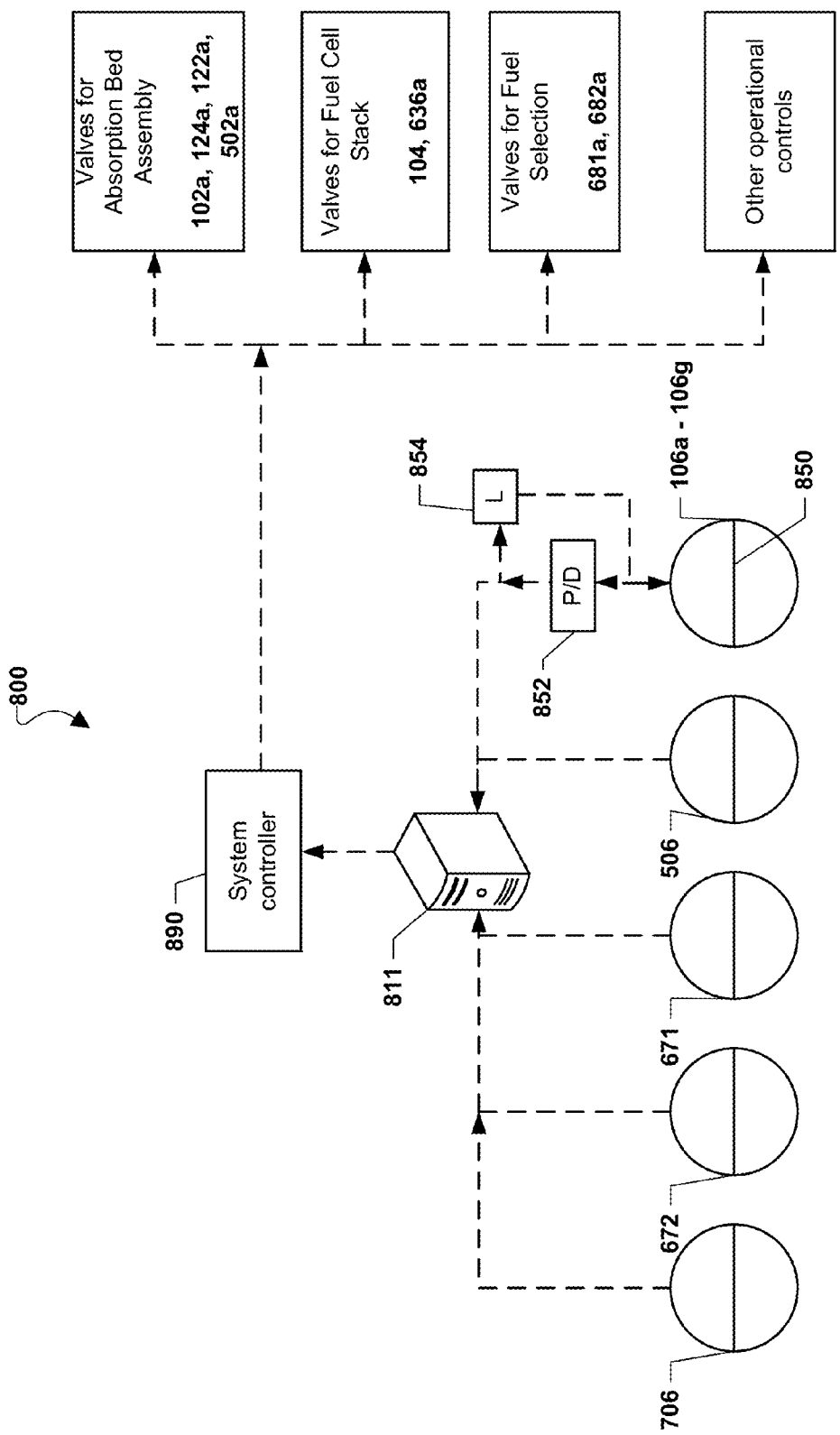
FIG. 8A schematically illustrates a detection system.

FIG. 8A illustrates a detection system to automatically alter system parameters (e.g., opening/closing valves, shutting off the fuel cell stack, etc.) based on detected undesirable constituents. Various detectors 106*a*-106*g*, 506, 672, 671, and/or 706 may be used to detect undesirable constituents at various locations in the fuel steam of a fuel cell system. Regardless of the exact location of the detectors, each detector may be any type suitable for detecting undesirable constituents such as oxygen, water, siloxanes, and sulfur.

In a particular embodiment, the detector(s) may be one or more color change detectors. Each color change detector includes a color change region, such as a color change pad 850 shown in FIG. 8A, which changes color after being exposed to a particular type of undesirable constituent. For example, a color change detector with a white detector pad may turn yellow when exposed to sulfur. The color change detector 106*a*-106*g*, 506, 672, 671, and/or 706 may have an optical component such as a color sensitive photodetector 852 and optionally a light source 854, which illuminates the pad. The optical component records the change in color and sends that information to a color change database 811. The color change database 811 collects the incoming color change data from the detectors 106*a*-106*g*, 506, 672, 671, and/or 706 and creates/updates a color change map, which determines the intensity of a particular undesirable constituent in the measured fuel stream. Based on the change in color received from a color change detector, the amount or intensity of the color change may be calibrated to predict the amount of a particular undesirable constituent in a fuel stream. Real-time data from the color change detectors 106a-106g, 506, 672, 671, and/or 706 may be sent to a system controller 890, which may alter system parameters such as valves in the sorbent bed assembly (i.e., fuel processing module), valves associated with the fuel cell stack (i.e., power generation module), valves for fuel selection, or any other operational controls such as shutting down portions of the fuel cell system. Some of the changes in system parameters were described above with respect to FIGS. 1-7, such as using a reserve sorbent bed upon detecting a breakthrough event (e.g., sulfur after the last primary sorbent bed).

Figure 8B:
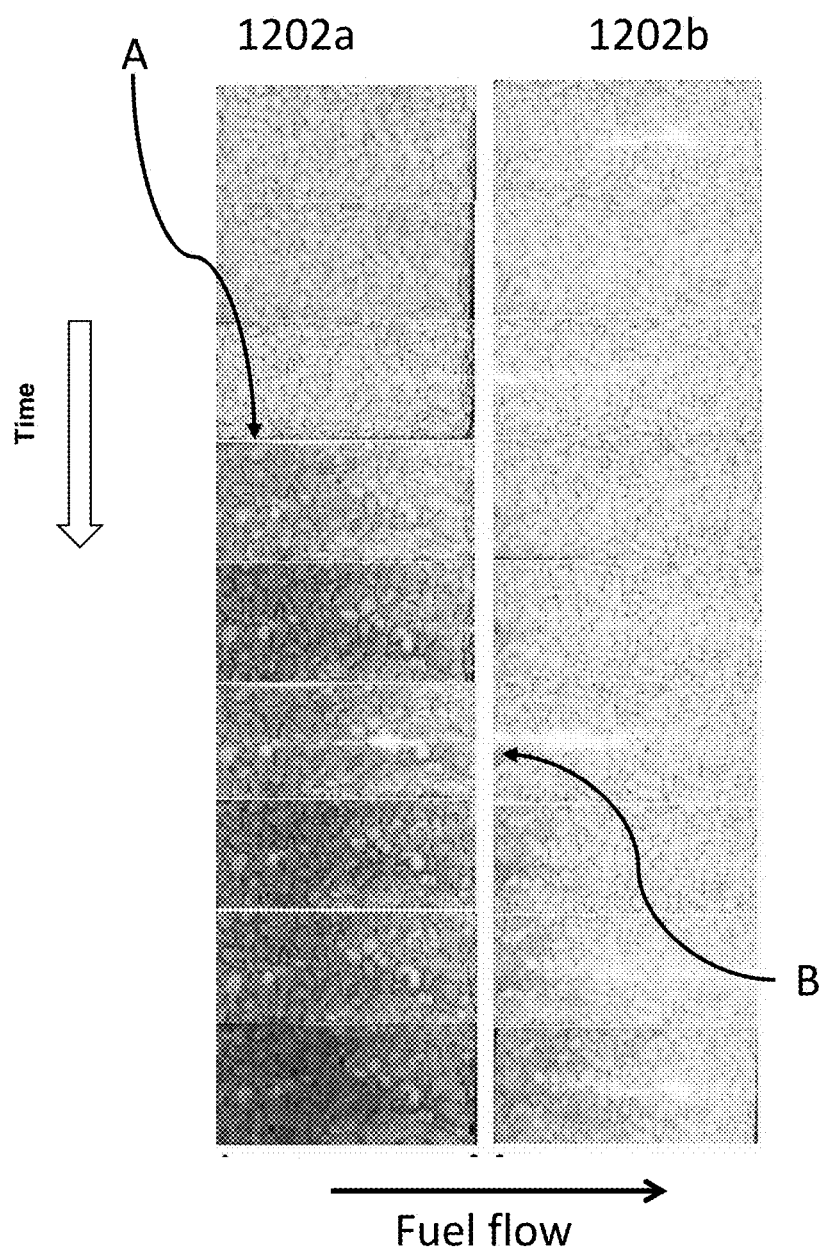
FIG. 8B is a set of images showing color changes that may occur in sensing materials suitable for use in the various embodiments.

FIG. 8B shows an example of the color changes that may occur in the sensing materials suitable for use in the various embodiments. Specifically, sensing material pad 1202a shown in column 1 is located in a detector 106a positioned after a first sorbent bed, while sensing material pad 1202b shown in column 2 is located in a detector 106a positioned after a second sorbent bed downstream of the first sorbent bed. Time lapse photographs of these same two sensing pads 1202a, 1202b are shown at nine sequential times, with the dark material on the left showing the presence of sulfur breakthrough, and the fuel flow from left to right. The actual color changes, which may indicate breakthroughs, are shown by points A and B (indicating breakthrough events from the first and second sorbent beds, respectively). That is, the color sensing material may change color based on the presence of one or more undesirable constituent (e.g., sulfur, etc.). For example, in some embodiments, the color change may involve turning from a light (e.g., light blue) to a dark (e.g., dark brown) color, or vice versa.

As an alternative, any of the detectors 106a-106g, 506, 672, 671, and/or 706 may detect undesirable constituents in the fuel stream by detecting the resistance change in a resistor associated with a particular undesirable constituent. A metal resistor (e.g., copper), which has not reacted with an undesirable constituent has a particular reference resistance. An undesirable constituent (e.g., sulfur) may react with a particular metal resistor (e.g., changing copper at least partially to copper sulfide) changing the resistivity of the resistor, thereby indicating an undesirable constituent is present. For example, a detector with a copper metal strip shaped resistor may have a relatively low resistivity. Organosulfur compounds present in the fuel stream may react with the copper resistor forming copper sulfide and increasing resistivity on the resistor strip, thereby indicating the presence of the undesirable constituent. Much like the color change detector system described above, resistivity changes may be mapped according to a particular undesirable constituent and the metal strip. As a further alternative embodiment, any of the detectors 106a-106g, 506, 672, 671, and/or 706 may use an artificial nose to detect a particular undesirable constituent or any number of undesirable constituents. Artificial noses may be calibrated to detect one or more undesirable constituents present in the fuel stream. An artificial nose comprises a reactive polymer tipped fiber optic channel. The polymer changes its optical properties (e.g., reflectance or refractive index) upon reacting with the undesirable constituent. Thus, light propagating in the channel and reflecting from the polymer tip has a different property than before the tip reacts with the undesirable constituent.

Figure 12A:
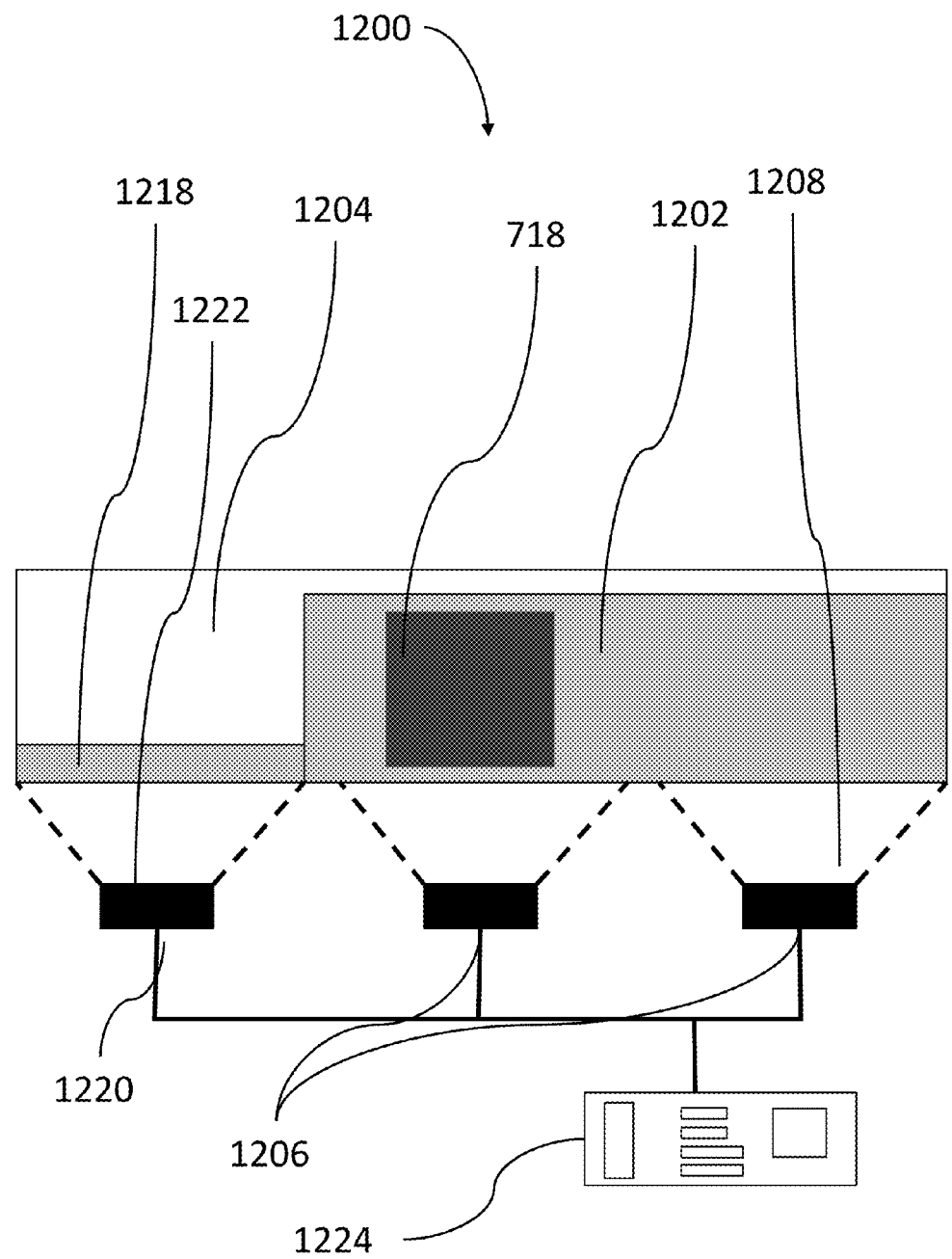
FIG. 12A illustrates a block diagram of an optical detector for detecting undesirable constituents.

In other embodiments, one or more of the detectors 106a-106g, 506, 672, 671 and/or 706 may be an optical detector 1200 as illustrated in FIG. 12A. In one embodiment, the optical detector 1200 includes a sensing material 1202 configured to change color in the presence of the undesirable constituents. The sensing material 1202 may be a color changing pad as described above in reference to FIG. 8A. The sensing material 1202 may be a paint or dye disposed on a substrate 1204. The paint or dye may change color upon exposure to an undesirable constituent. Alternatively, the sensing material 1202 may be a liquid or gel which changes color upon exposure to the undesirable component. Alternatively, the sensing material 1202 may be particles or granules which change color upon exposure to an undesirable constituent. These particles may be packed into a translucent housing to facilitate flow. In some embodiments, the sensing material 1202 is sulfur sensitive, such that it changes color upon exposure to sulfur or a sulfur containing compound. In other embodiments, the sensing material 1202 changes color upon exposure to another undesirable constituent, such as siloxanes, oxygen, or water. In some embodiments, the sensing material 1202 is sensitive to several different undesirable components. The sensing material 1202 may change to a distinct color upon exposure to each of the undesirable components. In some embodiments, the sensing material 1202 may be color change pellets made of a zeolite or mixed metal oxide through which the fuel flow may pass. In some embodiments, the optical detector 1200 includes at least one sensor 1206 configured to register the change in color of the sensing material 1202. In one embodiment, the at least one sensor 1206 is a plurality of sensors 1206. Each sensor may be disposed facing the sensing material 1202. For instance, when the sensing material 1202 is a paint or dye disposed on a substrate 1204, the at least one sensor 1206 may be disposed facing the substrate. Each of the at least one sensor 1206 may be a color change detector. The color change detector may include one or more color sensitive photodetectors. The color change detector may include a photodetector that detects the color blue, a photodetector that detects the color green, and/or a photodetector that detects the color red. The sensor 1206 may output each detected color change as a digital signal to the processor 1224 described below. Alternatively, the sensor 1206 may output each detected color change as an analogue output with varying direct current (DC) voltage. The sensor 1206 may output its signal via a wired or wireless signal, such as via a controlled area network (CAN) communication.

Some embodiments of the optical detector 1200 include a light source 1208 coupled to the sensor. The light source may illuminate the sensing material 1202 so that at least one sensor 1206 can detect the color of the sensing material 1202. In some embodiments, the at least one sensor 1206 may include one or more of red light, blue light, green light, and/or white light photodetector. The light source 1208 may be an electrical light source, such as a lamp or solid state lighting source. In some embodiments, the light source 1208 includes one or more light-emitting diodes (LEDs). The light source 1208 may be electrically coupled to a power regulating circuit (not shown) to ensure a constant luminous output, or to allow varied luminous output. Some embodiments include a plurality of light sources 1208.

Figure 12B:
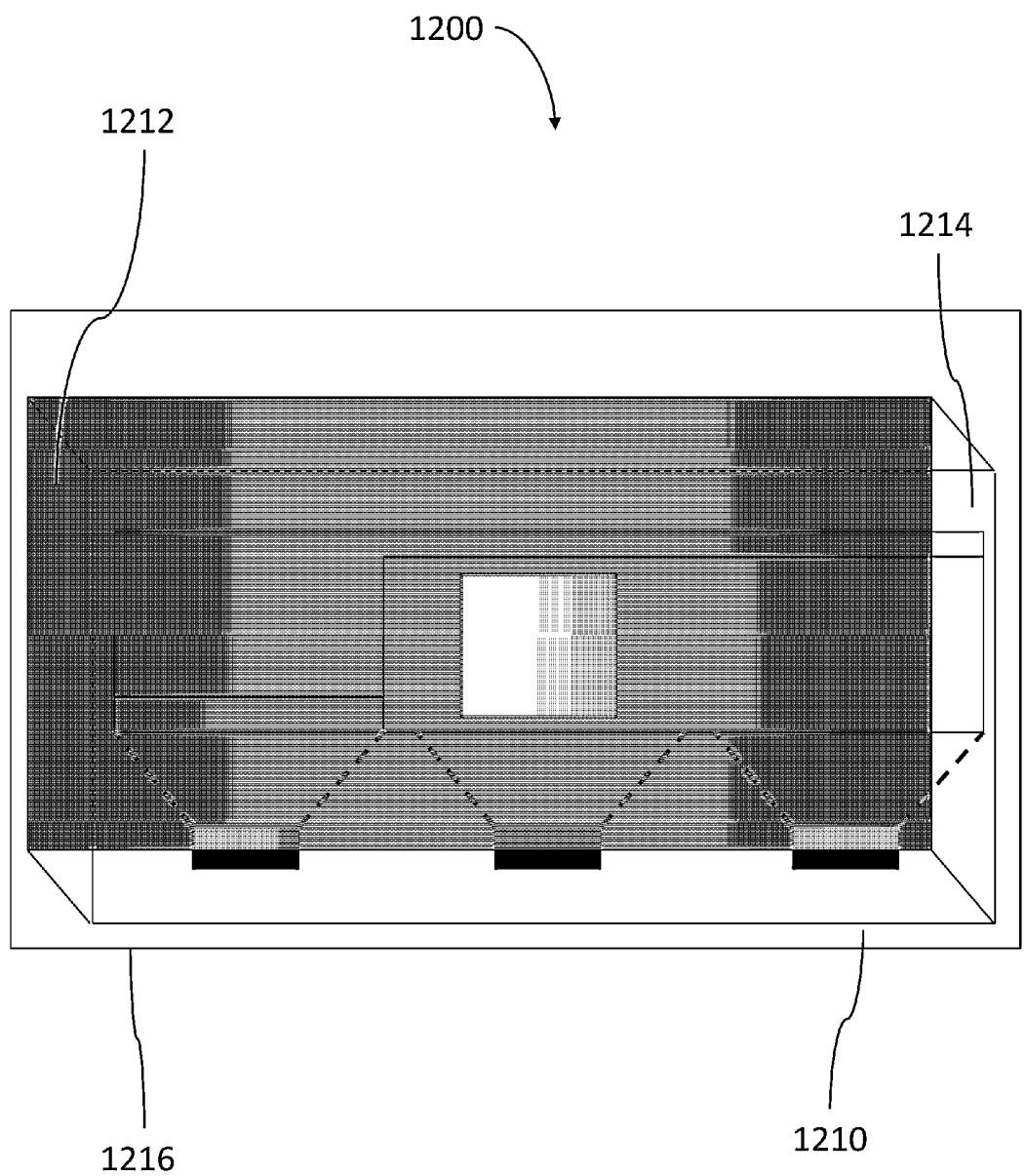
FIG. 12B illustrates a block diagram of an optical detector for detecting undesirable constituents, with a housing and casing.

Some embodiments of the optical detector 1200, as shown in FIG. 12B, include a housing 1210 as shown in FIG. 12B.

The housing 1210 may enclose the sensing material 1202, the at least one sensor 1206 and the light source(s) 1208. The housing 1210 may be substantially impervious to light. For instance, its exterior 1212 may be composed of material, such as a metal or plastic, which is substantially impervious to light. The exterior 1212 of the housing may be black, to prevent light passage. In some embodiments, a light-impervious housing 1210 prevents light leakage into or out of the housing 1210 exterior 1212, and improves the signal to noise ratio in the light perceived by the at least one sensor 1206. For instance, the light impervious housing 1210 may prevent a change in ambient light from causing the sensing material 1202 to appear to change color, causing the at least one sensor 1206 to register a false alarm. The interior 1214 of the housing 1210 may be a light color, such as white. In some embodiments, a light-colored interior 1214 spreads the light from the light sources 1208 to a greater extent, improving the operation of the optical detector 1200. Additional embodiments include an external casing 1216 surrounding the housing. The casing 1216 may be substantially impervious to light. In some embodiments, the casing 1216 and housing 1212 have one or more conduits (not shown) that permit gas to enter the optical detector 1200 without permitting light to enter. For instance, the conduits may have a plurality of bends such that the conduits reverse directions one or more times, effectively blocking the light out.

Referring again to FIG. 12A, the optical detector 1200 may include a reference material 1218. In some embodiments, the reference material 1218 does not change color given exposure to undesirable constituents. The reference material 1218 may be composed of any material described above for the sensing material. The reference material may be disposed upon the substrate 1204. In some embodiments, the reference material 1218 is substantially the same color as the sensing material 1202 absent undesirable components. The reference material 1218 may be composed of the same material as the sensing material 1202, but the reference material 1218 may have a transparent barrier (not shown) over material 1218 preventing the reference material 1218 from being exposed to undesirable components. Alternatively, the reference material 1218 may be composed of a material that does not change its color upon exposure to undesirable components, but which has the same color as the initial color of the sensing material 1202.

The optical detector 1200 may also include a reference sensor 1220 to sense a change in color of the reference material. The reference sensor may be constructed as described above for the at least one sensor 1206. The optical detector 1200 may also include a light source 1222 coupled to the reference sensor 1220. The light source 1222 may be any light source suitable for the light source 1208 described above. The light source 1222 may be coupled to the reference sensor 1220 and illuminating the reference material 1218 as described above in regard to the light source 1208. This reference sensor 1220 may be used to separate variations in signal due to environmental factors, such as ambient light or temperature, from variations in signal due to the presence of the fuel constituent intended to be detected.

In some embodiments, the optical detector 1200 is coupled to a processor 1224. The processor may be a valve controller and/or a system controller, as described above in reference to FIGS. 3A-8A. The processor 1224 may be a computing device 1000 as set forth in FIGS. 10 and 11 or a microprocessor. The processor 1224 may be a microprocessor. In some embodiments, the processor 1224 receives a signal from the at least one sensor 1206, and in response to the signal from at least one sensor 1206, records the color of the sensing material 1202. The processor 1224 may be configured to receive a signal from the reference sensor 1220, and in response to the signal from the reference sensor 1220 record the color of the sensing material 1206. In one embodiment, the processor 1224 is configured to subtract a value of a signal from the reference sensor 1220 from a value of a signal from the at least one sensor 1218 (e.g., a difference in values). This may have the effect of increasing a signal-to-noise ratio, such as when a door of the cabinet is opened or a false signal or other optical noise causes the reference color to appear different. The processor 1224 may be configured to apply a signal averaging algorithm to increase a signal-to-noise ratio of a signal corresponding to a change in color of the sensing material. In some embodiments, the processor 1224 may receive signals from one or more sensors 1206 in each of multiple optical detectors 1200, which may be added together. For example, a signal from a first optical detector 1200 may be added to a signal from a second optical detector 1200 that is farther downstream in the flow path. Such adding of signals from different detectors that are upstream and downstream from one another may linearize their summed signal response.

In some embodiments, the processor 1224 is configured to generate an alarm signal when an alarm criterion is met. The alarm criterion may be met when an absolute value of the value transmitted by any sensor 1206 to the processor 1224 deviates from a calibrated value of the sensor by more than a preset value. The preset value may correspond to a change in color indicating an unacceptable level of the undesirable constituent. In one embodiment, the alarm signal may be generated when a criterion is met for a predetermined amount of time. For instance, the processor 1224 may generate the alarm signal only if the value transmitted to the processor 1224 deviates from the calibrated value by more than a preset value for more than a preset period of time (e.g., for a longer period of time that a cabinet door is typically opened).

In another embodiment, the alarm signal is generated when a sensor value falls within predetermined alarm value range. For instance, the processor 1224 may ignore a sensor value that exceeds an upper threshold limit consistent with an improbable reading, as indicating a fault in the optical detector 1200 rather than a detection of the undesirable constituent. The alarm signal may be generated when any individual sensor value is over predetermined threshold value. As an example, where the at least one sensor 1206 includes at least one sensor configured to sense red light, at least one sensor configured to sense blue light, and at least one sensor configured to sense green light, the processor 1224 may generate an alarm if the signal from only the green light sensor exceeds a threshold value. Each sensor included in the at least one sensor 1206 may have a different threshold value stored by the processor 1224.

In some embodiments, the alarm signal may be generated when least squares regression coefficient(s) exceed a preset value and/or fall outside a preset range. In one embodiment, a least squares regression assumes a certain type of curve to fit to a set of data, such as the set of values conveyed by the at least one sensor 1206, and minimizes the error of the data with regard to that curve type, thereby matching the coefficient values of that curve fit. This method may effectively perform signal averaging as well as slope analysis simultaneously. Additionally, the least squares regression may analyze the quality of the fit by calculating a standard error of data points. This deviation, called the "R^2" value, may be utilized to dictate that unless the data is sufficiently well fit, an alarm signal should not be sent. Skilled practitioners in the art will be aware of many computation techniques for applying the least-squares algorithm.

In another embodiment, the alarm signal may be generated when the second derivative of sensor values with respect to time exceeds a preset value. For instance, the processor 1224 may fit a curve to a series of values received from the at least one sensor 1206 as measured against the passage of a period of time and calculate the second derivative of the curve. A second derivative exceeding a certain threshold may indicate that the rate at which the color of the sensor material 1202 is changing is accelerating, indicating an increasing proportion of the undesirable constituent passing through the optical detector 1200. Alternatively, the alarm signal may be generated when the first derivative of sensor values with respect to time exceeds a preset value. For instance, the processor 1224 may fit a curve to a series of values received from the at least one sensor 1206 as measured against the passage of a period of time and calculate the first derivative of the curve. A first derivative exceeding a certain threshold may indicate that the color of the sensor material 1202 is changing at a particular rate, indicating a certain volume of the undesirable constituent is passing through the optical detector 1200. The processor 1224 may be configured to differentiate between positive and negative slope of sensor signal variation. For instance, external light pollution may produce an increasingly positive detector value, evidenced by a positive first derivative with respect to time, whereas actual poison detection may produce an increasingly negative detector value, evidenced by a negative first derivative with respect to time. Skilled practitioners will be aware of many effective computation approaches to calculating first and second derivatives with respect to time given various datasets.

In another embodiment, the set of values conveyed by the at least one sensor 1206 may be fit to a sigmoid based function. For example, the sigmoid based function may be based on $f(x)=1/(1+e^{-x})$, and modified by various coefficients and additions. In an embodiment, the coefficients used to modify the base function may represent alarm thresholds for color change limits such that an alarm signal is generated when a color change received from at least one sensor 1206 requires a fit with coefficients exceeding a coefficient value threshold. Skilled practitioners in the art will be aware of many computation techniques for an algorithm using the sigmoid based function.

In additional embodiments, the alarm signal is generated when the sum of absolute values of sensor values exceeds a preset value. Thus, if the sensor 1206 senses red, blue, and green color change values, the processor 1224 may generate an alarm signal if any one value exceeds the threshold, or if no one value exceeds the threshold but the combination of values added together does. The processor 1224 may be configured to differentiate between positive and negative readback change of sensors 1206. The processor 1224 may be configured to apply a different alarm algorithm for each individual sensor 1206. For instance, in an embodiment as depicted in FIG. 3D, the processor 1224 may use an algorithm designed to generate an alarm quickly upon a perceived change in conditions, at the cost of a higher rate of false positives, for a sensor in an optical detector 1200 placed in the fuel line just before entry to the fuel cell stack to indicate a higher content of undesirable constituents in the fuel being provided to the system. Alternatively, the processor 1224 may use an algorithm that responds less quickly but assesses change over time (e.g., using first and/or second derivatives) to produce a lower rate of false positives in a sensor in an optical detector 1200 placed in the line between two primary sorbent beds because the second bed will absorb any sulfur which breaks through the first bed. The processor 1224 may use any combination of the above-described algorithms for alarm generation with any sensor 1206. As an example, multiple alarm algorithms may be running in parallel, and if a given number of those alarm criteria are met, then an alarm detection may be confirmed.

In additional embodiments, fuel flow through a main flow path (e.g., through one or more primary sorbent bed) may be compared to the flow through an optical detector 1200. To perform such comparison, measurements of the main path flow and of the sensor flow, based on either the instantaneous flow rate or on the total volume that has flowed through each path, may be taken. In various embodiments, a ratio of the main path flow to the sensor flow may be used as an indication of the number of total volumes the one or more primary sorbent bed has cycled through versus the number of total volumes the sensor material has cycled through. This ratio may be used to determine how degraded the sensor material should be compared to the one or more primary sorbent bed, thereby allowing the color change witnessed in the sensor material to be a reflection of the degradation of the one or more primary sorbent bed.

In various embodiments, an alarm threshold for the system may be developed based on the ratio between the flow in the main flow path and the flow in the sensor flow path. That is, at various flow ratios, there are various thresholds which if crossed indicate degraded health of the main flow sorbent beds. For example, if a system is operating with a flow ratio of 1 volume sensor flow to 1000 volumes main path flow, it may be found that the alarm should be raised if the value of discoloration registered by the sensor is greater than 100. For the same system, but with the flow ratio at 1 volume sensor flow to 2000 volumes main path flow, it may be found that the alarm should be raised if the value of discoloration registered by the sensor is greater than 130. Thus, in various embodiments, a system may have a flow ratio threshold function that dictates the allowable sensor value at any given flow ratio. Such allowable sensor values may be provided with respect to any number of parameters, including but not limited to detector value, detector value change since beginning of operation, detector slope, etc.

In some embodiments, signal characteristics of a particular sensor 1206 at a given time may be compared to those measured previously for the same sensor 1206. For example, a signal indicating the sensor 1206 detection of the color red in the sensing material at a given time may be compared to the signal indicating detection of the color red in the sensing material by that same sensor 1206 during its first several hours of operation. Further, in some embodiments the signal characteristics of a particular sensor 1206 measured at a given time may be compared to a color reference sample. For example, there may be a color calibration cartridge which is used to establish a baseline with any of the sensors 1206.

In another embodiment, the signals from a particular sensor 1206 may be processed to correct for variations in various operating conditions of the sensor 1206. Examples of several operating conditions which may change for the sensor 1206 are gas media flow rate, gas media temperature, gas media pressure, sensor temperature, sensor cabinet opened, to name a few. By correcting the sensor signal to a normalized value based on these varying operating conditions, false alarms can be avoided.

One or more optical detectors 1200 may be placed in a fuel cell assembly as described above in reference to FIGS. 2-8A. In some embodiments, the fuel cell assembly may include a fuel cell stack 105 as described above in reference to FIGS. 2-8A, and a fuel processing module, such as the fuel processing modules 280, 380a, 380b, 380c, 380d, 480a, 480b, 480c, 480d, 500, and/or 600 described above in reference to FIGS. 2-8A, fluidly connected to the fuel cell stack. The one or more optical detectors 1200 may be used as any of the detectors 106a-106g, 506, 672, 671 and/or 706 described above in reference to FIGS. 3A-8A. The one or more optical detectors 1200 may be used as components in any of the detectors 106a-106g, 506, 672, 671 and/or 706 described above in reference to FIGS. 3A-8A. Thus, the one or more optical detectors 1200, singly or in combination with additional detector elements, may be positioned in a fuel inlet line and/or in a slipstream line of the fuel cell system, as illustrated above in reference to FIG. 7. Where there is a plurality of optical detectors 1200, each detector 1200 may be positioned at a different location along a fuel inlet line of fuel cell system. The one or more optical detectors 1200, in combination with one or more processors 1224, may regulate one or more of the valves as described above in reference to FIGS. 2-8A, such as valves 102a, 104, 124a, 122a, 502a, 682a, 681a, and/or 636a. The one or more optical detectors 1200 and one or more processors 1224 may cause the valves to perform any action as described above in reference to FIGS. 2-8A.

Figure 12C:
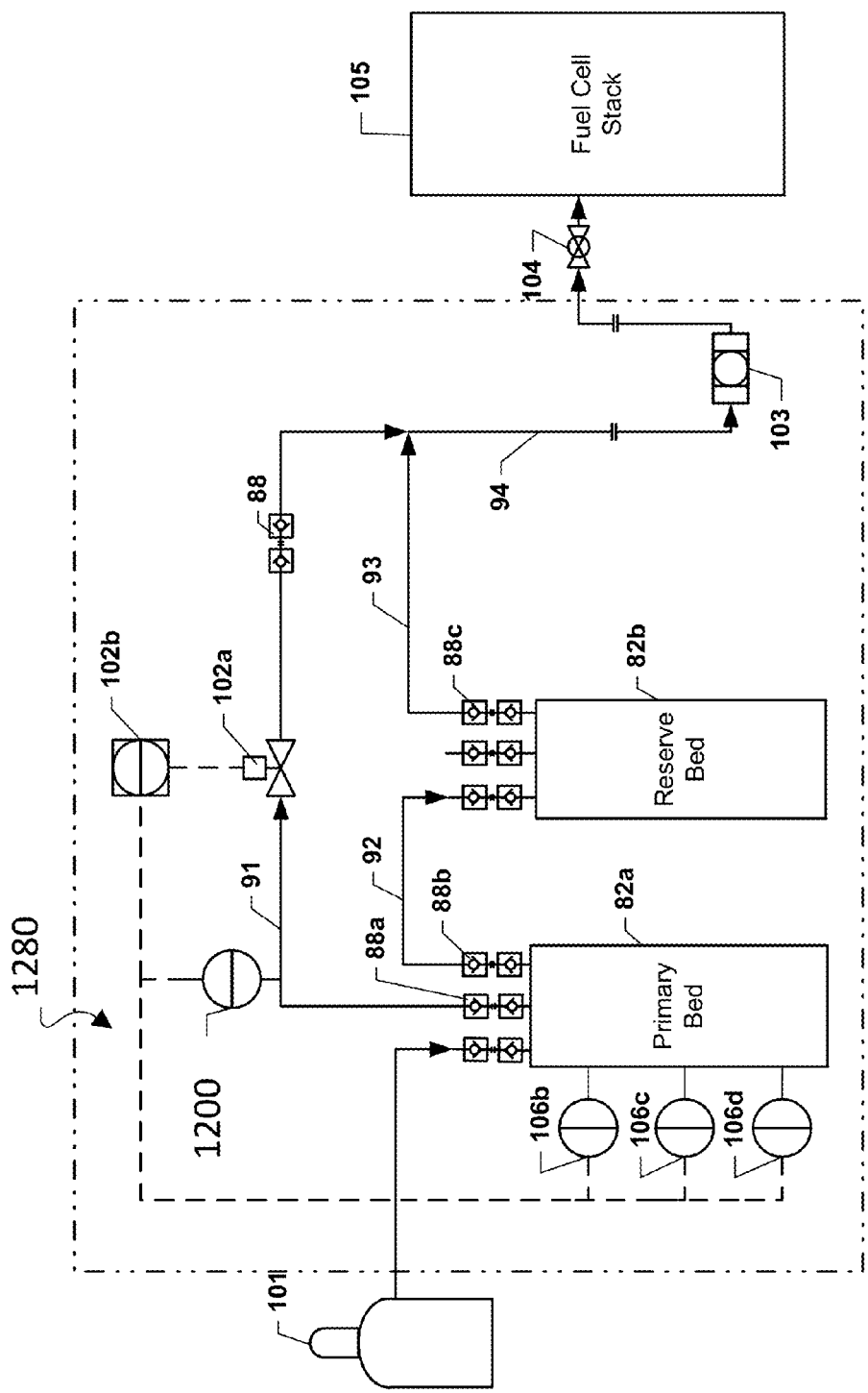
FIG. 12C illustrates an sorbent bed assembly with a an optical detector that may dictate fuel flow to the primary sorbent bed and the reserve sorbent bed.

As a non-limiting example, as depicted in FIG. 12C, a fuel cell assembly may include fuel cell stack 105, a fuel processing module 1280 fluidly connected to the fuel cell stack 105 and directing fuel to the fuel cell stack from a fuel source 101. The fuel processing module 1280 includes a primary sorbent bed 82a, a reserve sorbent bed 82b, a valve 102a configured to control fuel flow which bypasses the reserve sorbent bed 82b, and an optical detection system including one or more optical detectors 1200 as described above in reference to FIGS. 12A-B, for detecting undesirable constituents in the primary sorbent bed 82a. The open valve 102a is configured to direct all or a majority of fuel flow through the primary sorbent bed 82a bypassing the reserve sorbent bed 82b via conduit 91. Upon detection of the undesirable constituents, the valve 102a is closed to direct all fuel flow or partially closed to direct more fuel flow through the reserve sorbent bed 82b via conduit 92. The fuel processing module 1280 may use a bypass conduit 91 to direct fuel around the reserve sorbent bed 82b during steady state operation when valve 102a is open, as described above in reference to FIGS. 2-8A.

The fuel processing module 1280 may use additional conduits 92 and 93 to direct fuel through the reserve sorbent bed 82b when the valve 102a is closed, as described above in reference to FIGS. 2-8A. The fuel processing module 1280 may be connected to the fuel cell stack 105 via a fuel inlet conduit 94, which is regulated by an additional or failsafe valve 104 as depicted above in reference to FIGS. 2-8A. The various conduits and valves may connect to I/O connections 88, 88a-c. The fuel processing module 1280 may include additional detectors 106b, 106c, and 106d located on/in the primary sorbent bed 82a, as described above in reference to FIGS. 2-8A. The additional detectors 106b, 106c, and 106d may include optical detectors 1200 as described above in reference to FIGS. 12A-12B.

The valve 102a may be opened to direct a minority of fuel flow through the reserve sorbent bed 82b and a majority of fuel flow through the primary sorbent bed 82a before the alarm signal is generated. The valve 102a may be closed to direct all or a majority of fuel flow through the reserve sorbent bed 82b and none or a minority of fuel flow through the primary sorbent bed 82a when the alarm signal is generated. The valve 102a may be configured to direct all fuel flow through the primary sorbent bed 82a before the alarm signal has been generated if an additional valve in conduit 92 is closed and valve 102a is open. The valve 102a may be configured to direct all fuel flow through the reserve sorbent bed 82b when the alarm signal is generated and valve 102a is open.

FIG. 13 illustrates an embodiment method 1300 of detecting undesirable constituents in a fuel cell system. The method 1300 may include in step 1302 providing an optical detection system comprising a sensing material configured to change color in the presence of the undesirable constituents and at least one sensor configured to register the change in color of the sensing material. The sensor is coupled to a corresponding light source. The sensing material, the sensor and the light source are enclosed in a housing. In some embodiments, this is implemented as disclosed above in reference to FIGS. 12A-12B.

The method 1300 may include detecting an undesirable constituent in a fuel stream of the fuel cell system (step 1304). In some embodiments, the detection of the undesirable constituent may be implemented as disclosed above in reference to FIGS. 12A-12C.

The method 1300 may include generating an alarm signal when an alarm criterion is met (step 1306). In some embodiments, the detection of the undesirable constituent may be implemented as disclosed above in reference to FIGS. 12A-12C.

FIG. 14 illustrates another embodiment method 1400 of detecting undesirable constituents in a fuel cell system. The method 1400 may include in step 1402 providing an optical detection system comprising a sensing material configured to change color in the presence of the undesirable constituents and at least one sensor configured to register the change in color of the sensing material. The sensor is coupled to a corresponding light source. A reference material that does not change color in the presence of the undesirable constituents and a reference sensor configured to register the change in color of the reference material and optically coupled to a light source are also provided. In some embodiments, this is implemented as disclosed above in reference to FIGS. 12A-12C.

The method 1400 may further include detecting an undesirable constituent in a fuel stream of the fuel cell system (step 1404). In some embodiments, this is implemented as disclosed above in reference to FIGS. 12A-12C.

The method 1400 may further include generating an alarm signal when an alarm criterion is met (step 1406). In some embodiments, this is implemented as disclosed above in reference to FIGS. 12A-12C.

Figure 15:
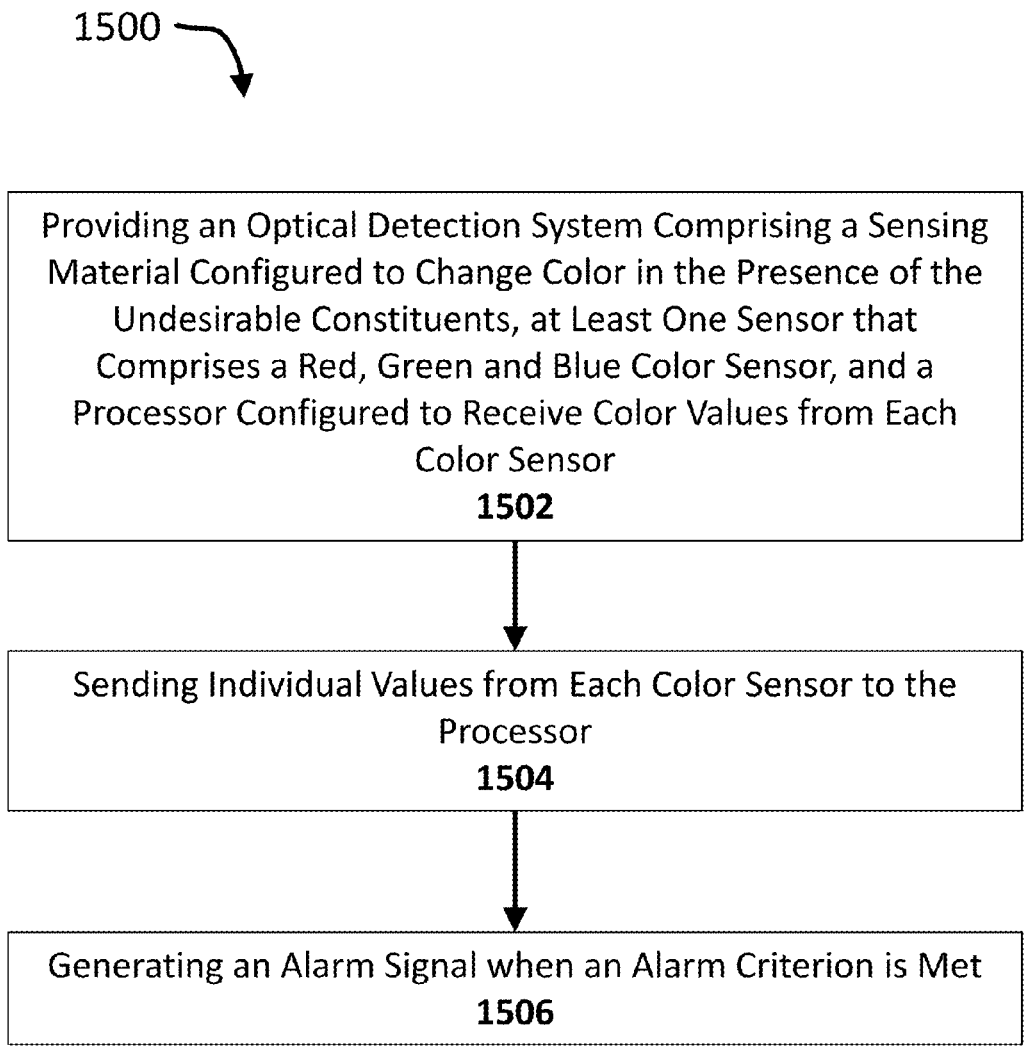
FIG. 15 is a flow chart illustrating a method of detecting undesirable constituents in a fuel cell system.

FIG. 15 illustrates another embodiment method 1500 of detecting undesirable constituents in a fuel cell system. The method 1500 may include a step 1502 of providing an optical detection system comprising a sensing material configured to change color in the presence of the undesirable constituents, at least one sensor that comprises a red, green and blue color sensor, and a processor configured to receive color values from each color sensor. In some embodiments, this is implemented as disclosed above in reference to FIGS. 12A-12B.

The method 1500 may include sending individual values from each color sensor to the processor (step 1504). In some embodiments, this is implemented as disclosed above in reference to FIGS. 12A-12C.

The method 1500 may include generating an alarm signal when an alarm criterion is met (step 1506). In some embodiments, this is implemented as disclosed above in reference to FIGS. 12A-12C.

Detection of breakthrough events/poisoning through performance measurements of the fuel cell stack.

Figure 9:
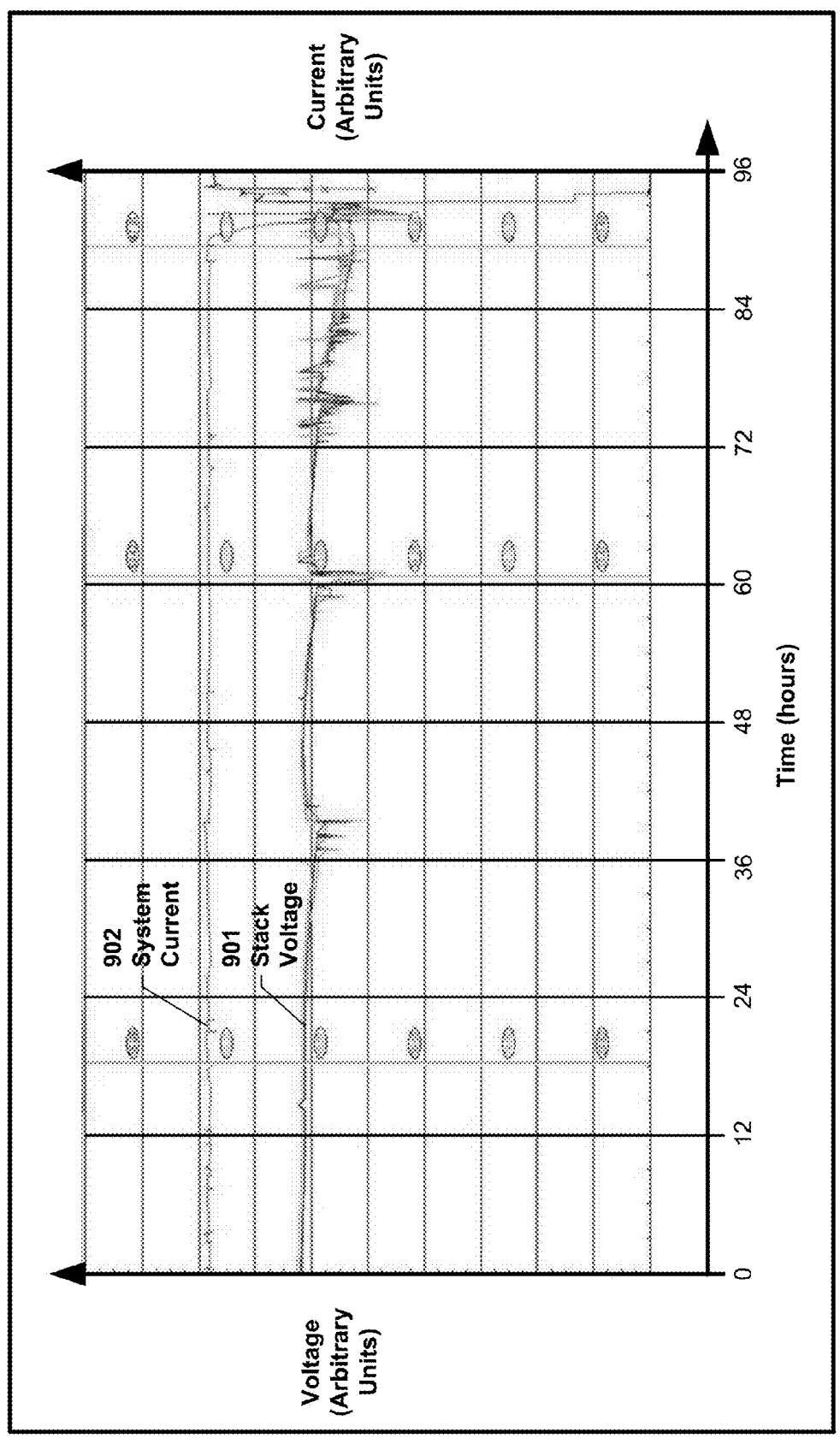
FIG. 9 is a plot of stack voltage and system current as a function of time to illustrate measured performance degradation of fuel cell stacks when exposed to an undesirable constituent.

FIG. 9 illustrates fuel cell performance measurements from several fuel cell stacks as the fuel cell stacks are poisoned with an undesirable constituent. In an embodiment, a monitor 110, as illustrated and described with reference to FIGS. 3A, 3D, 4A, 4D, and 6, may detect fuel cell poisoning in a fuel cell stack (or a breakthrough event causing fuel cell poisoning) by detecting degradations in fuel cell stack performance.

In the non-limiting illustration shown in FIG. 9, a monitor 110 may measure the individual stack voltages and/or the fuel cell system's current while operating the fuel cell stack 105 or the fuel cell system's current while operating a plurality of stacks 105. A fuel cell stack 105 may have a measured stack voltage 901 and a measured system current 902. FIG. 9 illustrates a slight drop in stack voltage of approximately 5.5% after about 36 hours of operation, roughly when the fuel cell stack is (or plurality of stacks are) exposed to sulfur. As shown, the current remains approximately constant at the time of fuel cell poisoning and after fuel cell poisoning from the undesirable constituent. Over the next few days, the stack voltage oscillates and eventually drops approximately to 15% of the original value at about 90 hours (or roughly two days after the initial exposure to sulfur.) At the same time, the system current crashes.

In an embodiment, a fuel cell stack monitoring system (e.g., monitor 110) may detect that a fuel cell stack 105 has been exposed to an undesirable constituent (e.g., sulfur) resulting from a breakthrough event when the fuel cell stack voltage decreases by at least 5% for a given fuel flow rate. Monitor 110, measuring about a 5% to 15% drop in voltage in conjunction with oscillations in stack voltage at constant system current for a given fuel flow rate, may also detect fuel cell poisoning or a breakthrough event attributable to poisoning from an undesirable constituent such as sulfur. Thus, remedial steps (e.g., shutting off the current draw from the fuel cell stack and shutting off fuel flow to the fuel cell stack, directing at least a portion of the fuel flow through a different sorbent bed, selecting a different fuel source, reducing fuel flow to the fuel cell stack, or other maintenance) may be conducted before the system experiences a crash in output current.

In various embodiments, an alarm signal may be generated based on fuel cell stack voltage and/or current values with respect to time. In some embodiments, a processor of the fuel cell stack monitoring system may fit a curve to a series of voltage and/or current values measured against the passage of a period of time and calculate the first and/or second derivative of the curve. For example, at least 5%, such as a 5% to 15% drop in voltage for a given fuel flow rate (e.g., over a given time period, such as in six hours or less, such as in three hours or less) and may be indicated if the first derivative goes below a threshold negative value (i.e., showing that the curve of voltage values is decreasing at a high rate). In another example, the oscillations in stack voltage may be indicated if the value of the first derivative of the fuel cell stack voltage measurements switches from positive to negative or vice versa, and/or the second derivative switches from a positive to negative value. (i.e., showing switches in concavity/curvature of the curve of the voltage values). In the various embodiments, skilled practitioners will be aware of many effective computation approaches to calculating first and second derivatives with respect to time given various datasets.

Example Desulfurization System.

In a non-limiting example, the optical detectors 1200 described above with reference to FIGS. 12A-12B may be part of a desulfurization system configured to perform a variety of functions related to a sorbent bed that removes various undesirable constituent sulfur species. In an embodiment, the desulfurization system may include at least one sorbent bed and at least one optical detector configured with at least one sulfur sensor.

In some embodiments, operation of the desulfurization system may be configured to provide sufficient time for procuring, scheduling and executing replacement of the at least one sorbent bed. In some embodiments, operation of the desulfurization system may minimize early replacement of the at least one sorbent bed, thereby maximizing sorbent bed utilization.

In various embodiments, an optical detector may be configured with two sulfur sensors, one of each being coupled to the inlet flow and outlet fuel flow of the optical detector. The two sulfur sensors may be optical sensors that monitor the color of a cartridge (e.g., a pad) that discolors in the presence of sulfur. In one example, the optical detector may be a SulfaTrack™ detector, which is sold commercially by SulfaTrap, Inc. for detection of very low levels of sulfur in gas phase systems. A SulfaTrack™ detector may provide visual indication of sulfur removal system breakthrough of <100 ppb. In some embodiments, a desulfurization system that includes a SufaTrack™ detector may provide real-time monitoring of sorbent bed performance and automated bed switching based thereon.

Testing of optical detectors may be performed to ensure that they properly detect breakthroughs of undesirable constituent for one or more sorbent bed. For example, in a desulfurization system configured with a first optical detector at the outlet of a first sorbent bed and a second optical detector at the outlet of a second sorbent bed. Each of the first and second optical detectors may be configured with a sulfur sensor coupled to the inlet flow and the outlet flow. Using a light source, the inlet and outlet sensors may sense sulfur based on a change in color (e.g., from white/clear to yellow, blue to brown, etc.). When an actual sulfur breakthrough event occurs (or is set-up for the purpose of testing), color sensing values at the inlet and outlet flows of each optical detector with respect to time may be compared to measured values of the actual fuel cell stack performance (e.g., voltage and/or current, such as shown in FIG. 9) with respect to the same time period. In this manner, correct detection of sulfur exposure may be verified if outlet sensor values changing rapidly correspond to a decrease in fuel cell stack performance attributable to sulfur exposure during the same time period.

Figure 8C:
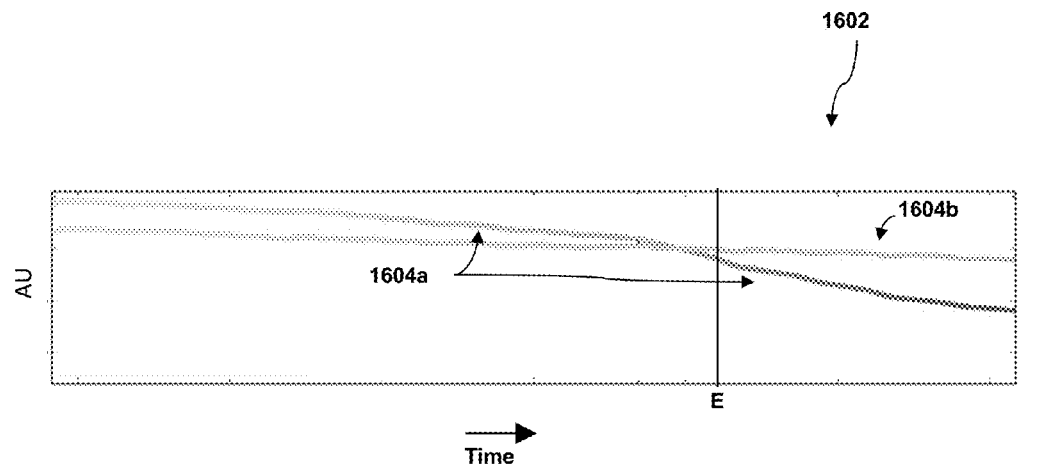
FIGS. 8C-8D illustrate plots of sensor values and fuel cell stack voltages as functions of time to test example optical detectors in a desulfurization system.
Figure 8D:
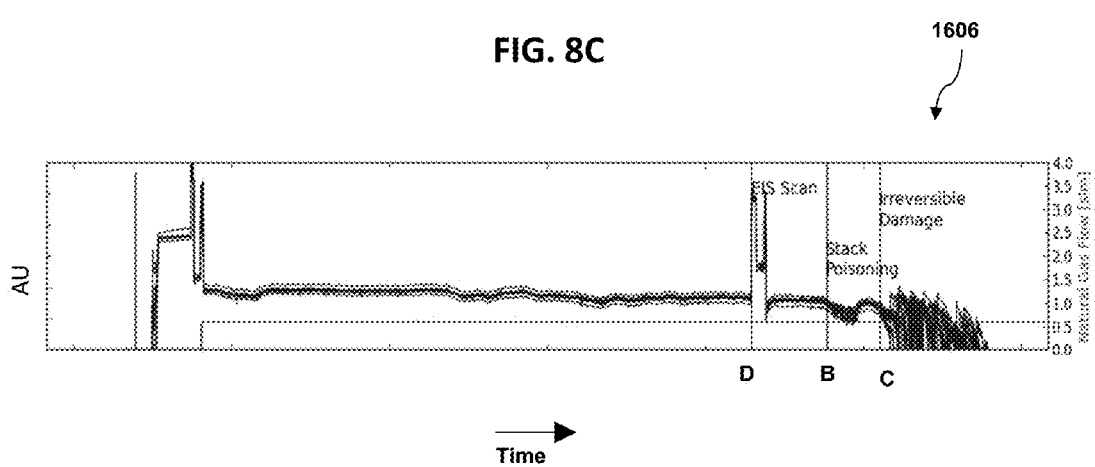

Examples of such comparisons for a desulfurization system are shown in the graphs of FIGS. 8C-8D. Graph 1602 corresponds to an output of an optical detector 1200 positioned at the outlet of the second sorbent bed in a two bed test setup. Line 1604a reflects color readings by the inlet sensor over time, and line 1604b reflects color readings by the outlet sensor over time. The data values 1604a, 1604b may be recorded as instances detecting white light plotted in the color sensed of the color change of the pad, similar to that shown in FIG. 8B. At time point E, the inlet sensor data values 1604a, 1604b may begin to indicate significant color change of the pad, which means that the fuel flow out of the second sorbent bed contains sulfur (i.e., sulfur breakthrough). Graph 1606 corresponds to fuel cell stack output voltage measurements over time, which shows performance loss (decrease in output voltage) due to sulfur breakthrough starting, for example, at point B shown in FIG. 8D. If it is found that a point E precedes point B by an expected window of time, the capability of the optical detection system to identify sulfur breakthrough may be verified. Thus, sorbent bed(s) 82a should be replaced and/or reserve bed(s) 82b should be activated after point E time but before point B in time. At point C, the stack suffers irreversible damage. Point D shows the effect of an electrochemical impedance spectroscopy test scan on the output voltage of the stack, the details of which are described in U.S. Pat. No. 8,652,697 and hereby incorporated by reference in its entirety.

Thus, in various embodiments, the detector 1200 may be used as a flow ratio based reflection of the health of the sorbent bed(s) 82, with point E identifying that the detector reading has registered a significant enough total discoloration (i.e., total data values 1604a, 1604b) to indicate that the health of sorbent bed(s) 82 requires action. In some embodiments, derivative functions may additionally or alternatively be used in calculations used to identify breakthrough events from sensor data values. For example, the inlet and outlet sensor data values 1604a, 1604b may be added to together to form a set of sum sensor data values (not shown). In various embodiments, first and/or second derivative(s) may be calculated for the sum sensor data values. A sulfur breakthrough may be detected and an alarm triggered if the first derivative and/or second derivative calculations go below a preset threshold value.

Computer Control Elements.

Control elements such as valve controllers 102b, 124b, 122b, 502b, 682b, 681b, 636b, monitor 110, system controller 890, and database 811 may be implemented using computing devices (such as computers) comprising processors, memory and other components that have been programmed with instructions to perform specific functions or may be implemented in processors designed to perform the specified functions. A processor may be any programmable microprocessor, microcomputer or multiple processor chip or chips that can be configured by software instructions (applications) to perform a variety of functions, including the functions of the various embodiments described herein. In some computing devices, multiple processors may be provided. Typically, software applications may be stored in the internal memory before they are accessed and loaded into the processor. In some computing devices, the processor may include internal memory sufficient to store the application software instructions.

Figure 10:
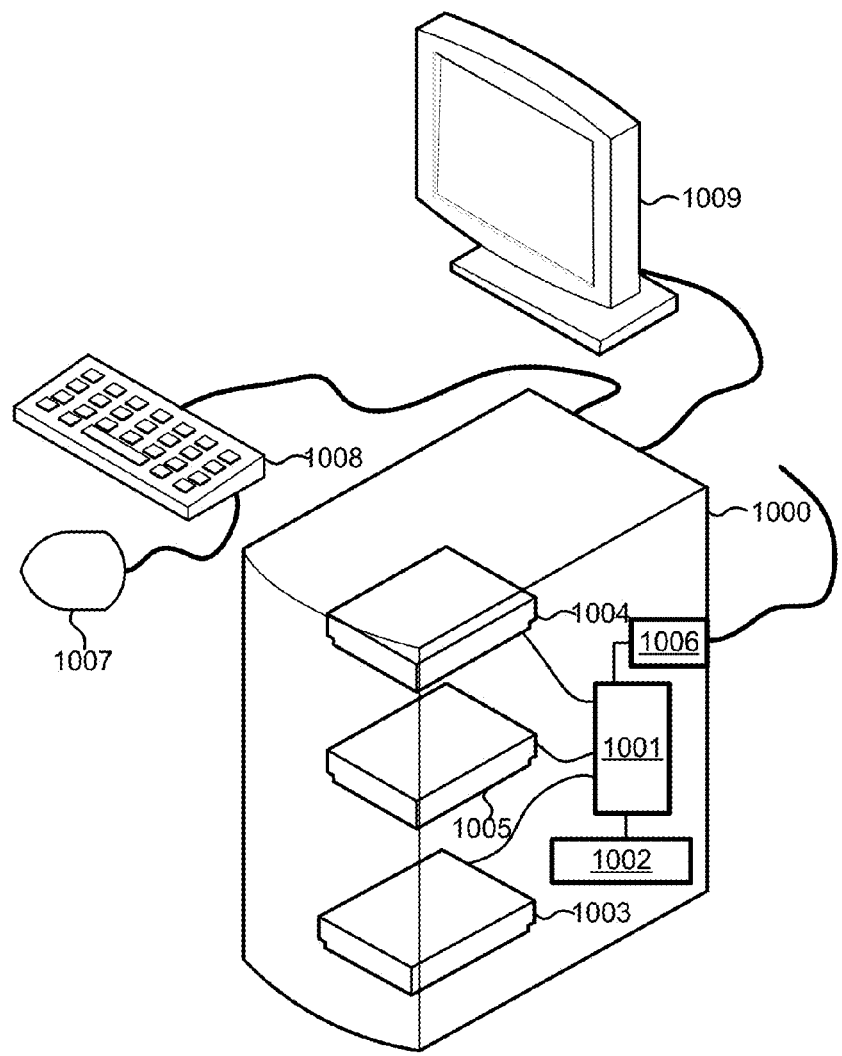
FIG. 10 illustrates a block diagram of a computing device suitable for use with any of the embodiments.

FIG. 10 is a block diagram of a computing device suitable for use with any of the embodiments. Such a computing device 1000 typically includes a processor 1001 coupled to volatile memory 1002 and a large capacity nonvolatile memory, such as a disk or solid state flash drive 1003. Typically, software applications may be stored in the internal memory 1002 before they are accessed and loaded into the processor 1001. The processor 1001 may include internal memory sufficient to store the application software instructions.

The computing device 1000 may also include a flash drive 1004 and a compact disc (CD) drive 1005 coupled to the processor 1001. Typically, the computing device 1000 will also include a pointing device such as a mouse 1007, a user input device such as a keyboard 1008 and a display 1009. The computing device 1000 may also include a number of connector ports 1006 coupled to the processor 1001 for establishing data connections or network connections or for receiving external memory devices, such as a USB or FireWire® connector sockets. In a notebook configuration, the computer housing includes the pointing device 1007, keyboard 1008 and the display 1009 as is well known in the computer arts.

While the computing device 1000 is illustrated as using a desktop form factor, the illustrated form is not meant to be limiting. For example, some or all of the components of computing device 1000 may be implemented as a desktop computer, a laptop computer, a mini-computer, a tablet, a smart phone or a personal data assistant.

Figure 11:
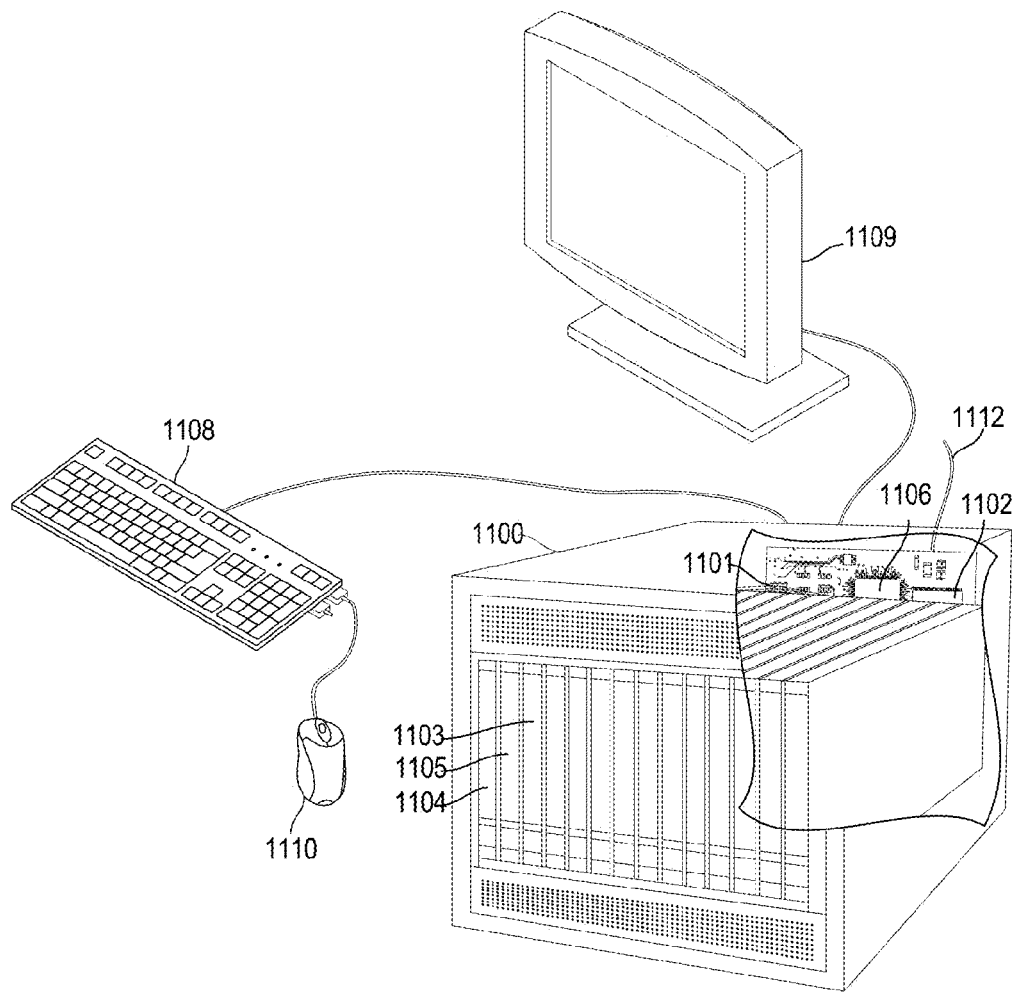
FIG. 11 illustrates a block diagram of a server-computing device suitable for use with any of the embodiments.

The various computing devices such as valve controllers 102b, 124b, 122b, 502b, 682b, 681b, 636b, monitor 110, system controller 890, and database 811 may also be implemented on any of a variety of commercially available server devices, such as the server 1100 illustrated in FIG. 11. Such a server 1100 typically includes a processor 1101 coupled to volatile memory 1102 and a large capacity nonvolatile memory, such as a disk drive 1103. The server 1100 may also include an external drive, compact disc (CD) or DVD disc drive 1104 coupled to the processor 1101. The server 1100 may also include network access ports 1106 coupled to the processor 1101 for establishing data connections with a network 1112, such as a local area network coupled to other broadcast system computers and servers. Servers 1100 may also include operator interfaces, such as a keyboard 1108, pointer device (e.g., a computer mouse 1110), and a display 1109.

The processors 1001 and 1101 may be any programmable microprocessor, microcomputer or multiple processor chip or chips that can be configured by software instructions (applications) to perform a variety of functions, including the functions of the various embodiments described below. In some mobile receiver devices, multiple processors may be provided, such as one processor dedicated to wireless communication functions and one processor dedicated to running other applications. Typically, software applications may be stored in the internal memory 1002, 1102, and or 1103 before they are accessed and loaded into the processors 1001 and 1101. The processor 1001 and 1101 may include internal memory sufficient to store the application software instructions.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some blocks or methods may be performed by circuitry that is specific to a given function.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

The invention claimed is:

1. A method of detecting undesirable constituents in a fuel cell system, comprising:
   providing an optical detection system comprising:
      a processor;
      a sensing material configured to change color in the presence of the undesirable constituents;
      constituent sensors disposed at different locations along a fuel inlet line of the fuel cell system and configured to register the change in color of the sensing material;
      a reference material configured to not change color in the presence of the undesirable constituents; and
      a reference sensor configured to register the change in color of the reference material;
   using the processor to detect an undesirable constituent in a fuel stream of the fuel cell system, by applying a different alarm detection algorithm to an output of each of the constituent sensors, the alarm detection algorithms being based on a difference between a change of color of the sensing material and the reference material; and
   generating an alarm signal when an alarm criterion of at least one of the alarm detection algorithms is met,
   wherein the alarm detection algorithms are selected from a least-squares threshold comparison algorithm, a first derivative threshold comparison algorithm, a second derivative threshold comparison algorithm, a sigmoid-based function threshold comparison algorithm, and an absolute value threshold comparison algorithm.

2. The method of claim 1, wherein the undesirable constituent comprises sulfur.

3. The method of claim 1, wherein the sensing material and the reference material each comprise paint or dye on a substrate, wherein each of the constituent sensors comprises a photodetector facing the substrate, and wherein illuminating the sensing material comprises illuminating the substrate.

4. The method of claim 2, wherein the constituent sensors include at least one red color sensor, at least one green color sensor, and at least one blue color sensor.

5. The method of claim 2, wherein at least one of the constituent sensors and a portion of the sensing material are positioned in a fuel inlet line or in a slipstream line of the fuel cell system.

6. The method of claim 2, wherein the alarm criterion of one of the detection algorithms is met when coefficients of a least squares regression of sensor values with respect to time fall outside a preset range.

7. The method of claim 2, wherein the alarm criterion of one of the detection algorithms is met when a first derivative, a second derivative, or a sum of absolute values of sensor values with respect to time falls outside a preset range.

8. The method of claim 2, wherein the generating the alarm signal comprises generating the alarm signal when the alarm criterion of at least two of the alarm detection algorithms is met.

9. The method of claim 2, wherein one of the detection algorithms comprises differentiating, by the processor, between a positive and negative slope of signal variation for at least one of the constituent sensors.

10. The method of claim 2, wherein:
   one of constituent sensors and the portion of the sensing material are disposed along the fuel inlet line upstream of a primary sorbent bed of the fuel cell system; and
   one of constituent sensors and a portion of the sensing material are located in the fuel inlet line downstream of the primary sorbent bed.

11. The method of claim 1, wherein the constituent sensors and the reference sensor are each coupled to a light source, and wherein the sensing material, the constituent sensors, the reference material, the reference sensor and the light sources are enclosed in a housing.

12. The method of claim 1, further comprising subtracting a value of a signal from the reference sensor from a value of a signal from the at least one of the constituent sensors to increase a signal-to-noise ratio for a signal corresponding to the change in color of the sensing material.

13. A method of controlling fuel flow to a sorbent bed in a fuel cell system, comprising:
   directing fuel through a primary sorbent bed to a fuel cell stack;
   diverting a portion of fuel entering the primary sorbent bed into a sensor configured to detect undesirable constituents exiting the primary sorbent bed;
   calculating a flow ratio based on a ratio of a total amount of fuel flowing through the primary sorbent bed to a total amount of fuel flowing through the sensor;
   determining an acceptable sensor value based on the calculated flow ratio;
   detecting a breakthrough event in the primary sorbent bed when a sensor value output from the sensor exceeds the acceptable sensor value; and
   directing fuel away from the primary sorbent bed in response to detecting the breakthrough event.

14. The method of claim 13, further comprising:
   directing at least a portion of the fuel flow through a reserve sorbent bed; and
   periodically bypassing the reserve sorbent bed, the reserve sorbent bed being external to a fuel processing module and larger than the primary sorbent bed.

15. The method of claim 13, wherein the sensor comprises at least one of a color change detector, a resistance change detector, and an artificial nose.

16. A method of controlling fuel flow to a sorbent bed in a fuel cell system, comprising:
- flowing fuel through a primary sorbent bed to a fuel cell stack;
- detecting a breakthrough event in the primary sorbent bed, by using a fuel cell stack performance monitoring system to detect an at least 5% decrease in a voltage of the fuel cell stack; and
- directing fuel away from the primary sorbent bed when the breakthrough event is detected.

* * * * *